United States Patent [19]

Teraji et al.

[11] Patent Number: 4,495,182
[45] Date of Patent: Jan. 22, 1985

[54] CEPHEM COMPOUNDS

[75] Inventors: Tsutomu Teraji, Osaka; Kazuo Sakane, Amagasaki; Jiro Goto, Suita, all of Japan

[73] Assignee: Fujisawa Pharmaceutical Co., Ltd., Osaka, Japan

[21] Appl. No.: 382,763

[22] Filed: May 27, 1982

[30] Foreign Application Priority Data

Jun. 22, 1981 [GB] United Kingdom ............... 8119173
Sep. 29, 1981 [GB] United Kingdom ............... 8129325
Apr. 26, 1982 [GB] United Kingdom ............... 8212051

[51] Int. Cl.³ ............... C07D 501/36; A61K 31/545
[52] U.S. Cl. ............... 514/226; 544/25; 544/27; 544/21
[58] Field of Search ............... 424/246; 544/25, 26, 544/27, 28, 21, 16

[56] References Cited

U.S. PATENT DOCUMENTS

| | | | |
|---|---|---|---|
| 4,242,510 | 12/1980 | Takaya et al. | 544/25 |
| 4,258,041 | 3/1981 | O'Callaghan et al. | 544/25 |
| 4,315,005 | 2/1982 | Ayres et al. | 424/246 |
| 4,332,798 | 6/1982 | Teraji et al. | 544/25 |
| 4,350,693 | 9/1982 | Takaya et al. | 424/246 |
| 4,381,299 | 4/1983 | Teraji et al. | 544/25 |

*Primary Examiner*—Nicholas S. Rizzo

*Attorney, Agent, or Firm*—Oblon, Fisher, Spivak, McClelland & Maier

[57] ABSTRACT

This invention relates to cephem compounds of high antimicrobial activity of the formula

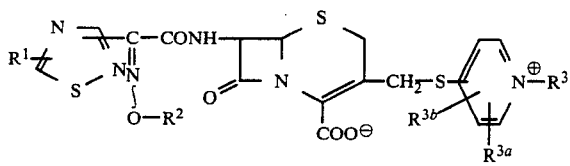

wherein
  $R^1$ is amino or a protected amino group;
  $R^2$ is hydrogen, lower aliphatic hydrocarbon group selected from lower alkyl, alkenyl and alkynyl which may be substituted with carboxy, protected carboxy, lower alkylthio or phenyl, cyclo(lower)alkyl, or cyclo(lower)alkenyl;
  $R^3$ is lower alkyl which may be substituted with carboxy, carbamoyl, hydroxy, amino or protected amino;
  $R^{3a}$ is hydrogen, lower alkyl or amino; and
  $R^{3b}$ is hydrogen or lower alkyl; and
pharmaceutically acceptable salts thereof.

31 Claims, No Drawings

CEPHEM COMPOUNDS

The present invention relates to new cephem compounds and pharmaceutically acceptable salts thereof. More particularly, it relates to new cephem compounds and pharmaceutically acceptable salts thereof, which have antimicrobial activities and to processes for preparation thereof, to pharmaceutical composition comprising the same, and to a method of using the same therapeutically in the treatment of infectious diseases in human being and animals.

Accordingly, it is one object of the present invention to provide new cephem compounds and pharmaceutically acceptable salts thereof, which are active against a number of pathogenic microorganisms.

Another object of the present invention is to provide processes for the preparation of new cephem compounds and pharmaceutically acceptable salts thereof.

A further object of the present invention is to provide pharmaceutical composition comprising, as active ingredients, said new cephem compounds and pharmaceutically acceptable salts thereof.

Still further object of the present invention is to provide a method for the treatment of infectious diseases caused by pathogenic bacteria in human being and animals.

The object new cephem compounds are novel and can be represented by the following general formula (I).

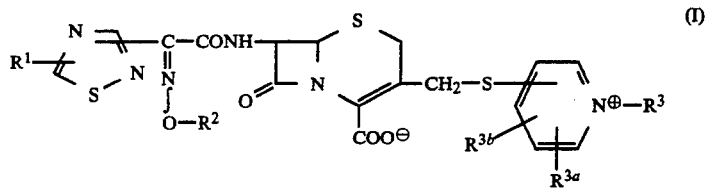

wherein
$R^1$ is amino or a protected amino group;
$R^2$ is hydrogen, lower aliphatic hydrocarbon group which may be substituted with suitable substituent(s), cyclo(lower)alkyl, or cyclo(lower)alkenyl;
$R^3$ is lower alkyl which may be substituted with suitable substituent(s);
$R^{3a}$ is hydrogen, lower alkyl or amino; and
$R^{3b}$ is hydrogen or lower alkyl.

According to the present invention, the new cephem compounds (I) can be prepared by processes which are illustrated in the following scheme.

Process 1

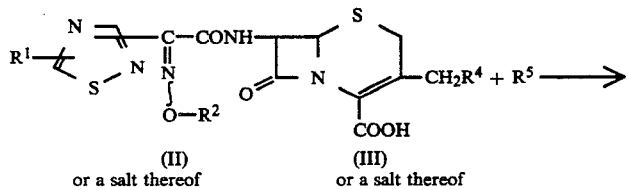

(II)
or a salt thereof (III)
or a salt thereof

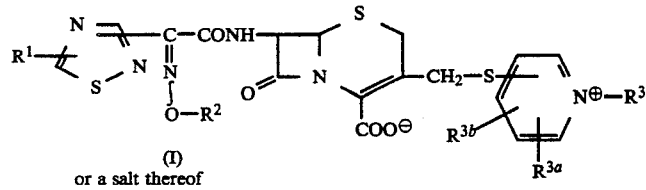

(I)
or a salt thereof

Process 2

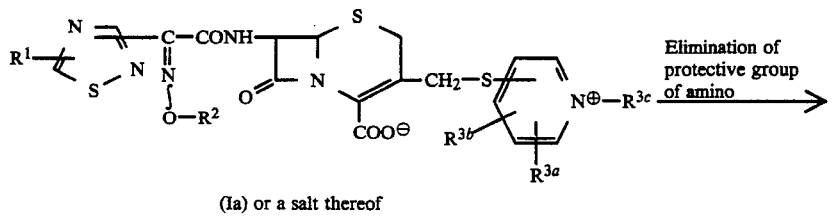

(Ia) or a salt thereof

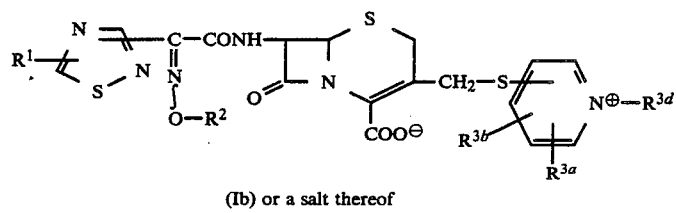
(Ib) or a salt thereof
Process 3
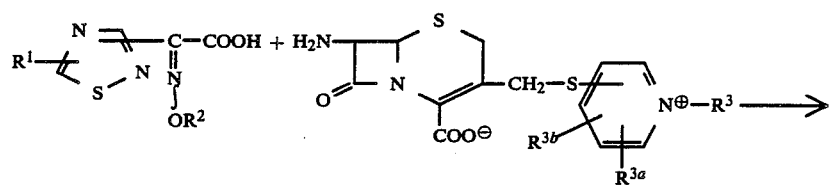
(IV)
or its reactive
derivative at the
carboxy group
or a salt thereof
(V)
or its reactive derivative
at the amino group or a
salt thereof
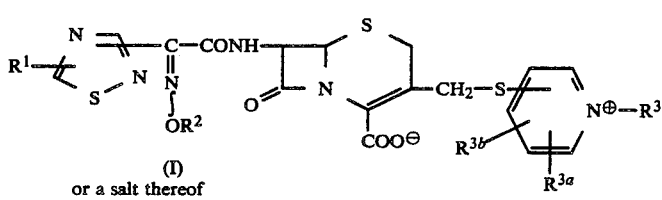
(I)
or a salt thereof
Process 4
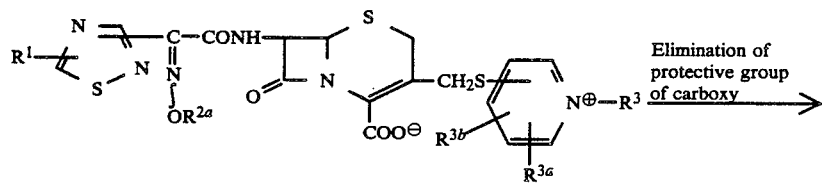
(Ic) or a salt thereof
Elimination of
protective group
of carboxy
(Id) or a salt thereof
Process 5
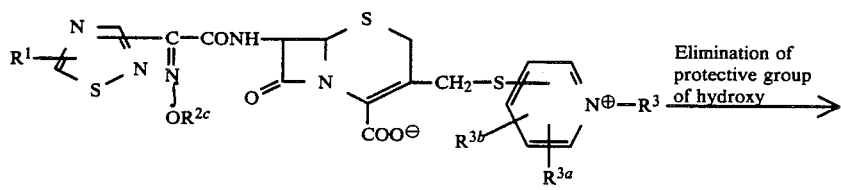
(Ie) or a salt thereof
Elimination of
protective group
of hydroxy -continued

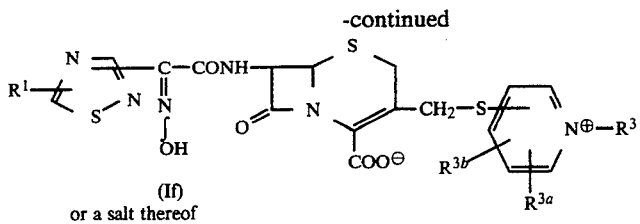

(If)
or a salt thereof wherein
$R^1$, $R^2$, $R^3$, $R^{3a}$ and $R^{3b}$ are each as defined above;
$R^4$ is a group which can be substituted with a group of the formula

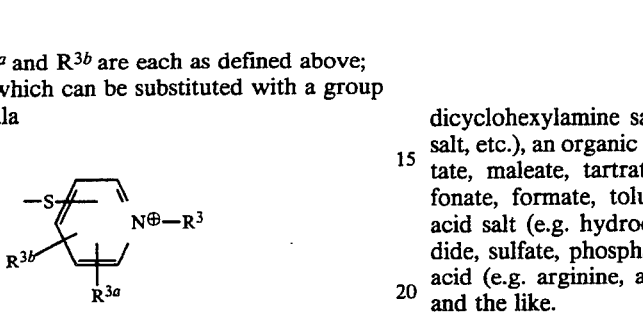

wherein
$R^3$, $R^{3a}$ and $R^{3b}$ are each as defined above;
$R^5$ is pyridthione having a group of the formula: $R^3$ on the nitrogen atom and having groups of the formulae: $R^{3a}$ and $R^{3b}$ on the carbon atoms, wherein $R^3$, $R^{3a}$ and $R^{3b}$ are each as defined above;
$R^{3c}$ protected amino(lower)alkyl;
$R^{3d}$ is amino(lower)alkyl;
$R^{2a}$ is protected carboxy(lower)alkyl;
$R^{2b}$ is carboxy(lower)alkyl; and
$R^{2c}$ is a protective group of hydroxy.

Regarding the object compounds (I), (Ia), (Ib), (Ic), (Id), (Ie) and (If) and starting compounds (II) and (IV), it is to be understood that said object and starting compounds include syn isomer, anti isomer and a mixture thereof. For example, with regard to the object compound (I), syn isomer means one geometrical isomer having the partial structure represented by the following formula:

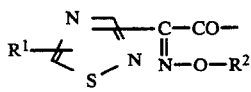

(wherein $R^1$ and $R^2$ are each as defined above) and anti isomer means the other geometrical isomer having the partial structure represented by the following formula:

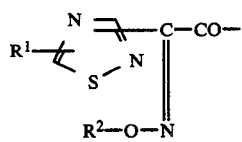

(wherein $R^1$ and $R^2$ are each as defined above).

Regarding the other compounds as mentioned above, the syn isomer and the anti isomer can also be referred to the same geometrical isomers as illustrated for the compound (I).

Suitable pharmaceutically acceptable salts of the object compounds (I) are conventional non-toxic salt and include a metal salt such as an alkali metal salt (e.g. sodium salt, potassium salt, etc.) and an alkaline earth metal salt (e.g. calcium salt, magnesium salt, etc.), an ammonium salt, an organic base salt (e.g. trimethylamine salt, triethylamine salt, pyridine salt, picoline salt, dicyclohexylamine salt, N,N'-dibenzylethylenediamine salt, etc.), an organic acid salt (e.g. acetate, trifluoroacetate, maleate, tartrate, methanesulfonate, benzenesulfonate, formate, toluenesulfonate, etc.), an inorganic acid salt (e.g. hydrochloride, hydrobromide, hydroiodide, sulfate, phosphate, etc.), or a salt with an amino acid (e.g. arginine, aspartic acid, glutamic acid, etc.), and the like.

In the above and subsequent descriptions of the present specification, suitable examples and illustrations of the various definitions which the present invention include within the scope thereof are explained in details as follows.

The term "lower" is intended to mean 1 to 6 carbon atoms, uless otherwise indicated.

Suitable "protected amino" and "protected amino" moiety in the term "protected amino(lower)alkyl" may include an acylamino or an amino group substituted by a conventional protecting group such as ar(lower)alkyl which may have at least one suitable substituent(s), (e.g. benzyl, trityl, etc.) or the like.

Suitable acyl moiety in the terms "acylamino" and "acyloxy" may include carbamoyl, aliphatic acyl group and acyl group containing an aromatic or heterocyclic ring. And, suitable examples of the said acyl may be lower alkanoyl (e.g. formyl, acetyl, propionyl, butyryl, isobutyryl, valeryl, isovaleryl, oxalyl, succinyl, pivaloyl, etc.);

lower alkoxycarbonyl having 2 to 7 carbon atoms (e.g. methoxycarbonyl, ethoxycarbonyl, propoxycarbonyl, 1-cyclopropylethoxycarbonyl, isopropoxycarbonyl, butoxycarbonyl, tertiarybutoxycarbonyl, pentyloxycarbonyl, hexyloxycarbonyl, etc.);

lower alkanesulfonyl (e.g. mesyl, ethanesulfonyl, propanesulfonyl, isopropanesulfonyl, butanesulfonyl, etc.); arenesulfonyl (e.g. benzenesulfonyl, tosyl, etc.); aroyl (e.g. benzoyl, toluoyl, xyloyl, naphthoyl, phthaloyl, indanecarbonyl, etc.);

ar(lower)alkanoyl (e.g. phenylacetyl, phenylpropionyl, etc.);

ar(lower)alkoxycarbonyl (e.g. benzyloxycarbonyl, phenethyloxycarbonyl, etc.), and the like.

The acyl moiety as stated above may have at least one suitable substituent(s) such as halogen (chlorine, bromine, fluorine and iodine), lower alkanoyl or the like.

Suitable acyl having substituent(s) may be lower alkanoyl(lower)alkanoyl (e.g., acetoacetyl, acetopropionyl, etc.).

Suitable lower aliphatic hydrocarbon group may include lower alkyl, lower alkenyl, lower alkynyl and the like.

Suitable "lower alkyl" and "lower alkyl" moiety in the term "lower alkyl which may be substituted with suitable substituent(s)" is one having 1 to 6 carbon atom(s) and may include methyl, ethyl, propyl, isopropyl, butyl, isobutyl, tert-butyl, pentyl, tert-pentyl, hexyl and the like, and preferably one having 1 to 4 carbon atom(s).

Suitable "lower alkenyl" is one having 2 to 6 carbon atoms and may include vinyl, allyl, isopropenyl, 1-propenyl, 2-butenyl, 3-pentenyl and the like, and preferably one having 2 to 4 carbon atoms.

Suitable "lower alkynyl" is one having 2 to 6 carbon atoms and may include ethynyl, 2-propynyl, 2-butynyl, 3-pentynyl, 3-hexynyl and the like, and preferably one having 2 to 4 carbon atoms.

The lower aliphatic hydrocarbon group as mentioned above may be substituted with 1 to 3 suitable substituent(s) such as carboxy, protected carboxy as mentioned below, halogen (e.g. chlorine, bromine, iodine, etc.), lower alkylthio (e.g. methylthio, ethylthio, propylthio, etc.), aryl (e.g., phenyl, tolyl, etc.) or the like.

Suitable "cyclo(lower)alkyl is one having 3 to 6 carbon atoms and may include cyclopropyl, cyclobutyl, cyclopentyl, cyclohexyl and the like, and preferably one having 5 to 6 carbon atoms.

Suitable "cyclo(lower)alkenyl" is one having 3 to 6 carbon atoms and may include cyclopropenyl, cyclobutenyl, cyclopentenyl, cyclohexenyl and the like, and preferably one having 5 to 6 carbon atoms.

Suitable substituent(s) on lower alkyl for $R^3$ may include carboxy, protected carboxy as mentioned below, hydroxy, amino, protected amino, carbamoyl, and the like.

Suitable "lower alkyl" moiety in the terms "protected amino(lower)alkyl", "amino(lower)alkyl", "protected carboxy(lower)alkyl" and "carboxy(lower)alkyl" can be referred to the ones as exemplified above.

Suitable $R^4$ may include an acid residue such as acyloxy, azido, halogen or the like, wherein acyl moiety in the term "acyloxy" and halogen can be referred to the ones as exemplified above.

Suitable "protected carboxy" and "protected carboxy" moiety in the term "protected carboxy(lower)alkyl" may include esterified carboxy in which said ester may be the ones such as alkyl ester (e.g. methyl ester, ethyl ester, propyl ester, isopropyl ester, butyl ester, isobutyl ester, t-butyl ester, pentyl ester, t-pentyl ester, hexyl ester, heptyl ester, octyl ester, nonyl ester, decyl ester, undecyl ester, dodecyl ester, hexadecyl ester, etc.), preferably lower alkyl ester;

lower alkenyl ester (e.g. vinyl ester, allyl ester, etc.);
lower alkynyl ester (e.g. ethynyl ester, propynyl ester, etc.); mono(or di or tri)-halo(lower)alkyl ester (e.g., 2-iodoethyl ester, 2,2,2-trichloroethyl ester, etc.);
lower alkanoyloxy(lower)alkyl ester (e.g. acetoxymethyl ester, propionyloxymethyl ester, 1-acetoxypropyl ester, valeryloxymethyl ester, pivaloyloxymethyl ester, hexanoyloxymethyl ester, 1-acetoxyethyl ester, 2-propionyloxyethyl ester, 1-isobutyryloxyethyl ester, etc.); lower alkanesulfonyl(lower)alkyl ester (e.g., mesylmethyl ester, 2-mesylethyl ester, etc.);
ar(lower)alkyl ester, for example, phenyl(lower)alkyl ester which may be substituted with one or more suitable substituent(s) (e.g. benzyl ester, 4-methoxybenzyl ester, 4-nitrobenzyl ester, phenethyl ester, trityl ester, diphenylmethyl ester, bis(methoxyphenyl)-methyl ester, 3,4-dimethoxybenzyl ester, 4-hydroxy-3,5-ditertiarybutylbenzyl ester, etc.);
lower alkoxycarbonyloxy(lower)alkyl ester (e.g. methoxycarbonyloxymethyl ester, ethoxycarbonyloxymethyl ester, ethoxycarbonyloxyethyl ester, etc.) which may be substituted with azido;
a heterocyclic ester, preferably benzotetrahydrofuryl ester which may be substituted with oxo group, more preferably phthalidyl ester;
aroyloxy(lower)alkyl ester (e.g. benzoyloxymethyl ester, benzoyloxyethyl ester, toluoyloxyethyl ester, etc.); aryl ester which may have one or more suitable substituent(s) (e.g. phenyl ester, tolyl ester, tertiarybutylphenyl ester, xylyl ester, mesityl ester, cumenyl ester, etc.), and the like.

Suitable protective group of hydroxy may include aforesaid acyl, ar(lower)alkyl (e.g. benzyl, trityl, etc.) and the like.

Preferred embodiments of the object compound (I) are as follows.

Preferred embodiment of $R^1$ is amino;

$R^2$ is hydrogen, lower alkyl, lower alkoxycarbonyl(lower)alkyl, carboxy(lower)alkyl, lower alkylthio(lower)alkyl, ar(lower)alkyl (more preferably triphenyl(lower)alkyl), lower alkenyl, lower alkynyl, cyclo(lower)alkyl or cyclo(lower)alkenyl;

$R^3$ is lower alkyl (most preferably methyl), hydroxy(lower)alkyl, carboxy(lower)alkyl, amino(lower)alkyl, carbamoyl(lower)alkyl or acylamino(lower)alkyl [more preferably lower alkoxycarbonylamino(lower)alkyl];

$R^{3a}$ is hydrogen, lower alkyl or amino; and
$R^{3b}$ is hydrogen or lower alkyl.

The processes for preparing the object compounds of the present invention are explained in details in the following.

Process 1

The object compound (I) or a salt thereof can be prepared by reacting the compound (II) or a salt thereof with the compound (III) or a salt thereof.

Suitable salt of the compound (II) can be referred to the ones exemplified for the compound (I).

Suitable salt of the compound (III) may include an alkali metal salt (e.g., sodium salt, potassium salt, etc.).

The present reaction may be carried out in a solvent such as water, phosphate buffer, acetone, chloroform, acetonitrile, nitrobenzene, methylene chloride, ethylene chloride, formamide, dimethylformamide, methanol, ethanol, ether, tetrahydrofuran, dimethylsulfoxide, or any other organic solvent which does not adversely affect the reaction, preferably in ones having strong polarities. Among the solvents, hydrophilic solvents may be used in a mixture with water. The reaction is preferably carried out in around neutral medium. When the compound (II) is used in a free form, the reaction is preferably conducted in the presence of a base, for example, inorganic base such as alkali metal hydroxide, alkali metal carbonate, alkali metal bicarbonate, organic base such as trialkylamine, and the like. The reaction temperature is not critical, and the reaction is usually carried out at ambient temperature, under warming or under heating. The present reaction is preferably carried out in the presence of alkali metal halide (e.g. sodium iodide, potassium iodide, etc.), alkali metal thiocyanate (e.g. sodium thiocyanate, potassium thiocyanate, etc.) etc.

Process 2

The object compound (Ib) or a salt thereof can be prepared by subjecting the compound (Ia) or a salt thereof to elimination reaction of the protective group of amino.

Suitable salts of the compounds (Ia) and (Ib) can be referred to the ones exemplified for the compound (I).

The present elimination reaction is carried out in accordance with a conventional method such as hydrolysis; reduction; a method by reacting the compound (Ia) wherein the protective group is acyl group with iminohalogenating agent and then with iminoetherifying agent, and, if necessry, subjecting the resulting compound to hydrolysis; or the like. The hydrolysis may include a method using an acid or base or hydrazine and the like. These methods may be selected depending on the kind of the protective groups to be eliminated.

Among these methods, hydrolysis using an acid is one of the common and preferable method for eliminating the protective group such as substituted or unsubstituted alkoxycarbonyl (e.g. t-pentyloxycarbonyl, t-butoxycarbonyl, etc.), alkanoyl (e.g. formyl, etc.), cycloalkoxycarbonyl, substituted or unsubstituted aralkoxycarbonyl (e.g. benzyloxycarbonyl, substituted benzyloxycarbonyl, etc.), ar(lower)alkyl (e.g. benzyl, trityl, etc.) or the like.

Suitable acid may include an organic or an inorganic acid, for example, formic acid, trifluoroacetic acid, benzenesulfonic acid, p-toluenesulfonic acid, hydrochloric acid and the like, and preferable acid is, for example, formic acid, trifluoroacetic acid, hydrochloric acid, etc. The acid suitable for the reaction can be selected according to the kind of protective group to be eliminated. When the elimination reaction is conducted with the acid, it can be carried out in the presence or absence of a solvent. Suitable solvent may include a conventional organic solvent, water or a mixture thereof. When trifluoroacetic acid is used, the elimination reaction may preferably be carried out in the presence of anisole.

The hydrolysis using hydrazine is commonly applied for eliminating the protective group, for example, succinyl or phthaloyl.

The hydrolysis with a base is preferably applied for eliminating acyl group, for example, haloalkanoyl (e.g. dichloroacetyl, trifluoroacetyl, etc.) etc. Suitable base may include, for example, an inorganic base such as alkali metal hydroxide (e.g. sodium hydroxide, potassium hydroxide, etc.), alkaline earth metal hydroxide (e.g. magnesium hydroxide, calcium hydroxide, etc.), alkali metal carbonate (e.g. sodium carbonate, potassium carbonate, etc.), alkaline earth metal carbonate (e.g. magnesium carbonate, calcium carbonate, etc.), alkali metal bicarbonate (e.g. sodium bicarbonate, potassium bicarbonate, etc.), alkali metal acetate (e.g. sodium acetate, potassium acetate, etc.), alkaline earth metal phosphate (e.g. magnesium phosphate, calcium phosphate, etc.), alkali metal hydrogen phosphate (e.g. disodium hydrogen phosphate, dipotassium hydrogen phosphate, etc.), or the like, and an organic base such as trialkylamine (e.g. trimethylamine, triethylamine, etc.), picoline, N-methylpyrrolidine, N-methylmorpholine, 1,5-diazabicyclo[4,3,0]non-5-ene, 1,4-diazabicyclo[2,2,-2]octane, 1,5-diazabicyclo[5,4,0]undecene-5 or the like. The hydrolysis using a base is often carried out in water, a conventional organic solvent or a mixture thereof.

Among the protective group, the acyl group can be generally eliminated by hydrolysis as mentioned above or by the other conventional hydrolysis. In case that the acyl group is halogen substituted-alkoxycarbonyl or 8-quinolyloxycarbonyl, they are eliminated by treating with a heavy metal such as copper, zinc or the like.

The reductive elimination is generally applied for eliminating the protective group, for example, haloalkoxycarbonyl (e.g. trichloroethoxycarbonyl, etc.), substituted or unsubstituted aralkoxycarbonyl (e.g. benzyloxycarbonyl, substituted benzyloxycarbonyl etc.), 2-pyridylmethoxycarbonyl, etc. Suitable reduction may include, for example, reduction with an alkali metal borohydride (e.g. sodium borohydride, etc.) and the like.

The reaction temperature is not critical and may be suitably selected in accordance with the kind of the protective group of the amino group and the elimination method as mentioned above, and the present reaction is preferably carried out under a mild condition such as under cooling, at ambient temperature or slightly elevated temperature.

The present reaction includes, within its scope, the case that the protected amino group for $R^1$ is transformed into the free amino group in the course of the elimination reaction as mentioned above or in the post-treatment of the reaction mixture of reaction product.

Process 3

The object compound (I) or a salt thereof can be prepared by reacting the compound (IV) or its reactive derivative at the carboxy group or a salt thereof with the compound (V) or its reactive derivative at the amino group or a salt thereof.

Suitable reactive derivative at the amino group of the compound (V) may include conventional reactive derivative used in amidation, for example, Schiff's base type imino or its tautomeric enamine type isomer formed by the reaction of the compound (V) with a carbonyl compound; a silyl derivative formed by the reaction of the compound (V) with a silyl compound such as bis(trimethylsilyl)acetamide, trimethylsilylacetamide or the like; a derivative formed by reaction of the compound (V) with phosphorus trichloride or phosgene, and the like.

Suitable salt of the compound (V) may include an acid addition salt such as an organic acid salt (e.g. acetate, maleate, tartrate, benzenesulfonate, toluenesulfonate, etc.) or an inorganic acid salt (e.g. hydrochloride, hydrobromide, sulfate, phosphate, etc.); a metal salt (e.g. sodium salt, potassium salt, calcium salt, magnesium salt, etc.); ammonium salt; an organic amine salt (e.g. triethylamine salt, dicyclohexylamine salt, etc.), and the like.

Suitable reactive derivative at the carboxy group of the compound (IV) may include an acid halide, an acid anhydride, an activated amide, an activated ester, and the like. The suitable example may be an acid chloride; an acid azide; a mixed acid anhydride with an acid such as substituted phosphoric acid (e.g. dialkylphosphoric acid, phenylphosphoric acid, diphenylphosphoric acid, dibenzylphosphoric acid, halogenated phosphoric acid, etc.), dialkylphosphorous acid, sulfurous acid, thiosulfuric acid, sulfuric acid, alkylcarbonic acid, aliphatic carboxylic acid (e.g. pivalic acid, pentanoic acid, isopentanoic acid, 2-ethylbutyric acid, acetic acid or trichloroacetic acid, etc.), alkanesulfonic acid (e.g. methanesulfonic acid, ethanesulfonic acid, propanesulfonic acid, etc.) or aromatic carboxylic acid (e.g. benzoic acid, etc.); a symmetrical acid anhydride; an activated amide with imidazole, dimethylpyrazole, triazole or tetrazole; or an activated ester (e.g. cyanomethyl ester, methoxymethyl ester, dimethyliminomethyl [(CH₃)₂N⁺=CH—] ester, vinyl ester, propargyl ester, p-nitrophenyl ester, 2,4-dinitrophenyl ester, trichlorophenyl ester, pentachlorophenyl ester, mesyl phenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, or an ester with N,N-dimethylhydroxylamine, 1-hydroxy-2-(1H)-pyridone, N-hydroxysuccinimide, N-hydroxyphthalimide or 1-hydroxy-6-chloro-1H-benzotriazole, and the like. These reactive derivatives can be optionally selected from them according to the kind of the compound (IV) to be used.

The salts of the compound (IV) may be salts with an inorganic base such as an alkali metal salts (e.g. sodium or potassium salt), or an alkaline earth metal salt (e.g. calcium or magnesium salt), a salt with an organic base such as trimethylamine, triethylamine, pyridine, a salt with an acid (e.g. hydrochloric acid or hydrobromic acid) or the like.

The reaction is usually carried out in a conventional solvent such as water, acetone, dioxane, acetonitrile, chloroform, methylene chloride, ethylene chloride, tetrahydrofuran, ethyl acetate, N,N-dimethylformamide, pyridine or any other organic solvent which does not adversely influence to the reaction. Among these solvents, hydrophilic solvents may be used in a mixture with water.

When the compound (IV) is used in free acid form or its salt form in the reaction, the reaction is preferably carried out in the presence of a conventional condensing agent such as N,N-dicyclohexylcarbodiimide; N-cyclohexyl-N'-morpholinoethylcarbodiimide; N-cyclohexyl-N'-(4-diethylaminocyclohexyl)carbodiimide; N,N-diethylcarbodiimide; N,N-diisopropylcarbodiimide; N-ethyl-N'-(3-dimethylaminopropyl)carbodiimide; N,N-carbonylbis(2-methylimidazole); pentamethylene-ketene-N-cyclohexylimine; diphenylketene-N-cyclohexylimine; ethoxyacetylene; ethyl polyphosphate; isopropyl polyphosphate; diethyl phosphorochloridite; phosphorus oxychloride; phosphorus trichloride; phosphorus pentachloride; thionyl chloride; oxalyl chloride; triphenylphosphine; N-ethyl-7-hydroxybenzisoxazolium fluoroborate; N-ethyl-5-phenylisoxazolium-3'-sulfonate; 1-(p-chlorobenzenesulfonyloxy)-6-chloro-1H-benzotriazole; so-called Vilsmeier reagent, for example (chloromethylene) dimethylammonium chloride produced by the reaction of dimethylformamide with thionyl chloride or phosgene, a compound produced by the reaction of dimethylformamide with phosphorus oxychloride, etc.; or the like.

The reaction may be also carried out in the presence of an inorganic or an organic base such as an alkali metal hydroxide, an alkali metal bicarbonate, alkali metal carbonate, alkali metal acetate, tri(lower)alkylamine, pyridine, N-(lower)alkylmorpholine, N,N-di(lower)alkylbenzylamine, N,N-di(lower)alkylaniline as exemplified below, or the like. When the base or the condensing agent is in liquid, it can be used also as a solvent. The reaction temperature is not critical, and the reaction is usually carried out under cooling or at ambient temperature.

In the present reaction, a syn-isomer of the object compound (I) can be obtained preferably by conducting the reaction of the compound (V) with a syn isomer of the starting compound (IV).

Process 4

The object compound (Id) or a salt thereof can be prepared by subjecting the compound (Ic) or a salt thereof to elimination reaction of the protective group of carboxy.

Suitable salt of the compounds (Ic) and (Id) can be referred to the ones exemplified for the compound (I).

The present reaction is carried out in accordance with a conventional method such as hydrolysis, reduction or the like.

In case that the protective group is an ester, the protective group can be eliminated by hydrolysis. Hydrolysis is preferably carried out in the presence of a base or an acid including Lewis acid. Suitable base may include an inorganic base and an organic base such as an alkali metal (e.g. sodium, potassium, etc.), an alkaline earth metal (e.g. magnesium, calcium, etc.), the hydroxide or carbonate or bicarbonate thereof, trialkylamine (e.g. trimethylamine, triethylamine, etc.), picoline,1,5-diazabicyclo[4,3,0]none-5-ene, 1,4-diazabicyclo[2,2,-2]octane, 1,8-diazabicyclo[5,4,0]-undecene-7, or the like. Suitable acid may include an organic acid (e.g. formic acid, acetic acid, propionic acid, trichloroacetic acid, trifluoroacetic acid, etc.) and an inorganic acid (e.g. hydrochloric acid, hydrobromic acid, sulfuric acid, etc.). The elimination using Lewis acid such as trihaloacetic acid (e.g. trichloroacetic acid, trifluoroacetic acid, etc.) or the like is preferably carried out in the presence of cation trapping agents (e.g. anisole, phenol, etc.).

The reaction is usually carried out in a solvent such as water, an alcohol (e.g. methanol, ethanol, etc.), a mixture thereof or any other solvent which does not adversely influence to the reaction. A liquid base or acid can be also used as the solvent. The reaction temperature is not critical and the reaction is usually carried out under cooling to warming.

Reduction can be applied preferably for elimination of the protective group such as 4-nitrobenzyl, 2-iodoethyl, 2,2,2-trichloroethyl, or the like. The reduction method applicable for the elimination reaction may include, for example, reduction by using a combination of a metal (e.g. zinc, zinc amalgam, etc.) or a salt of chrome compound (e.g. chromous chloride, chromous acetate, etc.) and an organic or inorganic acid (e.g. acetic acid, propionic acid, hydrochloric acid, etc.); and conventional catalytic reduction in the presence of a conventional metallic catalyst (e.g. palladium-carbon, etc.).

Process 5

The object compound (If) or a salt thereof can be prepared by subjecting the compound (Ie) or a salt thereof to elimination reaction of the protective group of hydroxy.

Suitable salt of the compound (Ie) can be referred to the ones as exemplified for the compound (II).

The present elimination reaction can be carried out according to substantially the same manner as that of acidic hydrolysis in Process 4.

Thus obtained compounds according to Processes 1 to 5 as above may be converted into pharmaceutically acceptable salts thereof by conventional manner.

The object compound (I) of the present invention exhibits high antimicrobial activity and inhibits the growth of a number of microorganisms including pathogenic Gram-positive and Gram-negative bacteria.

For therapeutic administration, the cephalosporin compounds according to the present invention are used in the form of pharmaceutical preparation which contain said compounds in admixture with a pharmaceutically acceptable carriers such as an organic or inorganic solid or liquid excipient suitable for oral, parenteral or external administration. The pharmaceutical preparations may be in solid form such as capsule, tablet, dragee, ointment or suppository, or in liquid form such as solution, suspension, or emulsion. If desired, there may be included in the above preparations auxiliary substances, stabilizing agents, wetting or emulsifying agents, buffers and other commonly used additives.

While the dosage of the compounds may vary from and also depend upon the age and condition of the patient, an average single dose of about 50 mg., 100 mg., 250 mg., and 500 mg. of the compounds according to the present invention may be effective for treating of infectious diseases caused by a number of pathogenic bacteria. In general amounts, daily dose between 1 mg/body and about 1000 mg/body or even more may be administered.

Now in order to show the utility of the object compounds (I), test data on anti-microbial activity of representative compounds of the present invention are shown below.

Test method

One loopful of an overnight culture of each test strain in Trypticase-soy broth ($10^8$ viable cells per ml.) was streaked on heart infusion agar (HI-agar) containing graded concentrations of antibiotics, and the minimal inhibitory concentration (MIC) was expressed in terms of μg/ml after incubation at 37° C. for 20 hours.

Test Compound (1) 7-[2-Ethoxyimino-2-(5-amino-1;2,4-thiadiazol-3-yl)-acetamido]-3-(1-methyl-4-pyridiniothiomethyl)-3-cephem-4-carboxylate (syn isomer).
(2) 7-[2-Carboxymethoxyimino-2-(5-amino-1,2,4-thiadiazol-3-yl)acetamido]-3-(1-methyl-4-pyridiniothiomethyl)-3-cephem-4-carboxylate (syn isomer).
(3) 7-[2-Ethoxyimino-2-(5-amino-1,2,4-thiadiazol-3-yl)acetamido]-3-(1-methyl-2-pyridiniothiomethyl)-3-cephem-4-carboxylate (syn isomer).

| | Test Results | | |
|---|---|---|---|
| | Test Compound M.I.C. (μg/ml) | | |
| Test Bacteria | (1) | (2) | (3) |
| E. Coli NIHJ JC-2 | 0.10 | 0.10 | 0.10 |
| Kl. pneumoniae 12 | 0.10 | 0.05 | 0.10 |
| Pr. vulgaris 2 | 0.10 | 0.20 | 0.20 |

Preparation 1

To a solution of ethylenediamine (4.8 g) in ethanol (50 ml) was added 2,6-dimethylpyran-4-thione (2.8 g) and the mixture was stirred for 1.5 hours at room temperature. A resulting precipitate was filtered, washed with diethyl ether and dried to give 1-(2-aminoethyl)-2,6-dimethylpyrid-4-thione (2.5 g), mp. 162° to 164° C.

IR (Nujol): 3350, 3150, 1610, 1535, 1280, 1090 cm$^{-1}$.

NMR (DMSO-d$_6$, δ): 2.00 (6H, s), 2.80 (2H, t, J=6 Hz), 3.94 (2H, t, J=6 Hz), 7.00 (2H, s).

Preparation 2

The following compounds were obtained according to a similar manner to that of Preparation 1.

(1) 1-(2-Hydroxyethyl)-2,6-dimethylpyrid-4-thione, mp. 168° to 170° C.

IR (Nujol): 3250, 1610, 1530, 1380, 1275, 1090 cm$^{-1}$.

NMR (D$_2$O, δ): 2.50 (6H, s), 3.90 (2H, t, J=6 Hz), 4.35 (2H, t, J=6 Hz), 7.30 (2H, s).

(2) Sodium 1-carboxylatomethyl-2,6-dimethylpyrid-4-thione, mp. 208° to 201° C. (dec.).

IR (Nujol): 3300, 3100, 1620, 1600, 1540, 1380, 1270, 1090 cm$^{-1}$.

NMR (D$_2$O, δ): 2.35 (6H, s), 4.67 (2H, s), 7.30 (2H, s).

Preparation 3

To a solution of 1-(2-aminoethyl)-2,6-dimethylpyrid-4-thione (1.82 g) in 33% aqueous dioxane (15 ml) was added a solution of 2-t-butoxycarbonyloxyimino-2-phenylacetonitrile (2.5 g) in dioxane (15 ml) and the mixture was stirred for 1.5 hours at room temperature. The reaction mixture was evaporated to dryness and the residue was triturated in isopropyl alcohol to give 1-(2-t-butoxycarbonylaminoethyl)-2,6-dimethylpyrid-4-thione (2.2 g), mp. 175° to 178° C.

IR (Nujol): 3250, 1695, 1600, 1270, 1250, 1170, 1090 cm$^{-1}$.

NMR (CD$_3$COCD$_3$+D$_2$O, δ): 1.40 (9H, s), 2.50 (6H, s), 3.46 (2H, t, J=6 Hz), 4.24 (2H, t, J=6 Hz), 7.10 (2H, s).

Preparation 4

A mixture of 2-chloro-3-aminopyridine (12.8 g) and methyl iodide (56.8 g) was allowed to stand overnight in dark place at room temperature. To the mixture was added ethanol (20 ml) and the precipitates were collected by filtration, washed with diisopropyl ether and dried to give 1-methyl-2-chloro-3-aminopyridinium iodide (15.5 g), mp. 165° to 167° C. (dec.).

IR (Nujol): 3350, 3250, 3150, 1620, 1580, 1490 cm$^{-1}$.

NMR (D$_2$O, δ): 4.27 (3H, s), 7.43–7.90 (2H, m), 8.13 (1H, dd, J=2 and 5 Hz).

Preparation 5

A mixture of 2-chloropyridine (16 g) and methyl bromoacetate (72 g) was allowed to stand for one week at room temperature and then heated for 7 hours at 60° C. The resulting precipitates were collected by filtration and washed with diethyl ether to give 1-methoxycarbonylmethyl-2-chloropyridinium bromide (17.43 g), mp. 163° to 165° C.

IR (Nujol): 1745, 1610, 1565, 1495 cm$^{-1}$.

NMR (D$_2$O, δ): 3.90 (3H, s), 5.80 (2H, s), 8.0–9.2 (4H, m).

Preparation 6

A mixture of 1-methyl-2-chloro-3-aminopyridinium iodide (5.4 g) and sodium hydrosulfide (5.6 g) in methanol (100 ml) was stirred for one hour at room temperature and evaporated to dryness. The residue was triturated in cold water, filtered and dried to give 1-methyl-3-aminopyrid-2-thione (2.5 g), mp. 98° to 100° C.

IR (Nujol): 3400, 3300, 1610, 1580, 1530 cm$^{-1}$.

NMR (DMSO-d$_6$, δ): 3.90 (3H, s), 5.87 (2H, broad s), 6.43–6.83 (2H, m), 7.52 (1H, dd, J=2 and 6 Hz).

Preparation 7

The following compound was obtained according to a similar manner to that of Preparation 6. 1-Methoxycarbonylmethylpyrid-2-thione, mp. 90° to 92° C.

IR (Nujol): 1750, 1625, 1535 cm$^{-1}$.

NMR (CDCl$_3$, δ): 3.80 (3H, s), 5.20 (2H, s), 6.50–6.83 (1H, m), 7.03–7.40 (1H, m), 7.5–7.8 (2H, m).

Preparation 8

A mixture of 1-methoxycarbonylmethylpyrid-2-thione (4.2 g), 1N aqueous sodium hydroxide (30 ml) and methanol (30 ml) was stirred for 20 minutes at room temperature and evaporated to remove methanol. The aqueous solution was diluted to 100 ml with water and passed through an ion exchange resin "Dowex 50W-8, H-form (Trademark: prepared by the Dow Chemical Co., Ltd.)(56 ml). A precipitate from the eluate was collected by filtration to give 2.24 g of 1-carboxymethylpyrid-2-thione. The evaporation of the filtrate afforded the further crops (1.41 g) of the same compound. mp. 178° to 180° C.

IR (Nujol): 2700, 2530, 1718, 1624, 1535 cm$^{-1}$.

NMR (CD$_3$COCD$_3$, δ): 5.33 (2H, s), 6.43–6.97 (2H, m), 7.13–7.70 (2H, m), 7.90–8.17 (1H, m).

Preparation 9

A mixture of 1-methoxycarbonylmethylpyrid-2-thione (2.0 g) and conc. ammonium hydroxide (12 ml) in methanol (20 ml) was stirred for 2.5 hours at room temperature. The resulting precipitates were collected by filtration, washed with water and dried to give 1-carbamoylmethylpyrid-2-thione (1.42 g), mp. 240° to 245° C. (dec.).

IR (Nujol): 3360, 3200, 1663, 1613, 1580, 1530 cm$^{-1}$.

Preparation 10

To a solution of 1-methoxycarbonylmethylpyrid-2-thione (3.9 g) in methanol (40 ml) was added portionwise sodium borohydride (4.03 g) over 2 hours at room temperature. The mixture was evaporated and the residue was dissolved in a mixture of ethyl acetate (200 ml) and a saturated aqueous solution (100 ml) of sodium chloride. The organic layer was separated out and the aqueous layer was extracted with ethyl acetate (100 ml). The combined organic solution was washed with a saturated aqueous solution of sodium chloride, dried over magnesium sulfate and evaporated to dryness. The residue was purified by column chromatography on silica gel (50 g) using ethyl acetate as an eluent to give 1-(2-hydroxyethyl)pyrid-2-thione (1.87 g), mp. 95° to 97° C.

IR (Nujol): 3250, 1610, 1535 cm$^{-1}$.

Preparation 11

To a solution of pyran-4-thione (3.8 g) in acetone (27 ml) was added a solution of ethanolamine (2.07 g) in acetone (3.8 ml) and the mixture was stirred for 30 minutes at room temperature and cooled in an ice bath. A resulting precipitate was filtered, washed with acetone and dried to give 1-(2-hydroxyethyl)pyrid-4-thione (2.56 g), mp. 150° to 155° C. (dec.).

IR (Nujol): 3130, 2700, 1630, 1520 cm$^{-1}$.

NMR (D$_2$O, δ): 3.83–4.10 (2H, m), 4.17–4.43 (2H, m), 7.52 (2H, d, J=7 Hz), 7.78 (2H, d, J=7 Hz).

EXAMPLE 1

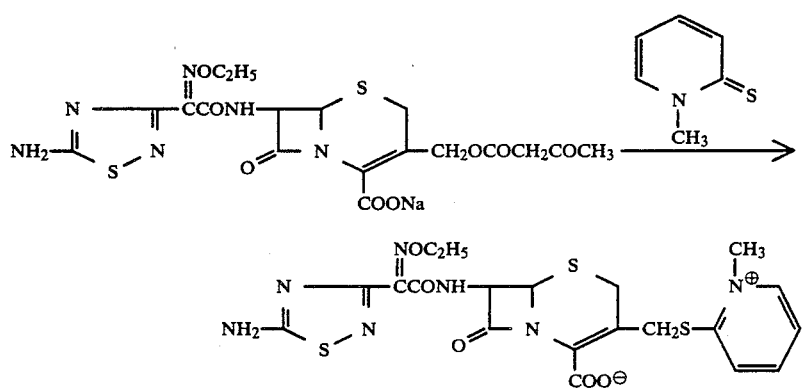

To a mixture of 1-methylpyrid-2-thione (0.6 g) and sodium iodide (6.0 g) in water (2 ml) was added sodium 7-[2-ethoxyimino-2-(5-amino-1,2,4-thiadiazol-3-yl)acetamido]-3-acetoacetoxymethyl-3-cephem-4-carboxylate (syn isomer) (2.14 g) at 55° to 60° C. under stirring, which was continued for 1.5 hours at the same temperature. The reaction mixture was cooled to ambient temperature, followed by an addition of a mixture of ethyl acetate (60 ml) and water (60 ml). The mixture was adjusted to pH 2.3 with 1N hydrochloric acid, and the aqueous layer was separated out and washed with ethyl acetate. The aqueous layer was evaporated to remove ethyl acetate and subjected to column chromatography on a non ionic adsorption resin Diaion HP 20 (Trademark: prepared by Mitsubishi Chemical Industries) (60 ml). After the column was washed with water, the elution was carried out with 30% aqueous methanol. The eluates containing an object compound were collected, evaporated to remove methanol under reduced pressure and lyophilized to give 7-[2-ethoxyimino-2-(5-amino-1,2,4-thiadiazol-3-yl)acetamido]-3-(1-methyl-2-pyridiniothiomethyl)-3-cephem-4-carboxylate (syn isomer) (910 mg), mp. 125° to 130° C. (dec.).

I.R. (Nujol): 3280, 3150, 1760, 1665, 1610, 1560, 1530, 1490 cm$^{-1}$.

N.M.R. (CD$_3$OD+D$_2$O, δ): 1.33 (3H, t, J=7 Hz), 3.52 and 3.73 (2H, ABq, J=18 Hz), 4.25 (3H, s), 4.33 (2H, q, J=7 Hz), 4.0–4.67 (2H, m), 5.15 (1H, d, J=5 Hz), 5.78 (1H, d, J=5 Hz), 7.43–8.83 (4H, m).

EXAMPLE 2

7-[2-Carboxymethoxyimino-2-(5-amino-1,2,4-thiadiazol-3-yl)acetamido]cephalosporanic acid trifluoroacetate (syn isomer) (2.24 g) and 1-methylpyrid-4- thione (550 mg), were reacted in the presence of sodium iodide (6.0 g), sodium bicarbonate (920 mg) and water (2 ml) according to a similar manner to that of Example 1 to give 7-[2-carboxymethoxyimino-2-(5-amino-1,2,4-thiadiazol-3-yl)-acetamido]-3-(1-methyl-4-pyridiniothiomethyl)-3-cephem-4-carboxylate (syn isomer) (770 mg), mp. 155° to 160° C. (dec.).

I.R. (Nujol): 3290, 3180, 1765, 1670, 1630, 1600, 1550, 1520, 1495 cm$^{-1}$.

N.M.R. (DMSO-$d_6$+$D_2O$, δ): 3.50 (2H, broad s), 4.17 (3H, s), 4.23–4.83 (4H, m), 5.03 (1h, d, J=5 Hz), 5.70 (1H, d, J=5 Hz), 8.02 (2H, d, J=7 Hz), 8.53 (2H, d, J=7 Hz).

EXAMPLE 3

The following compounds were obtained according to similar manners to those of aforesaid Examples.

(1) 7-[2-Ethoxyimino-2-(5-amino-1,2,4-thiadiazol-3-yl)acetamido]-3-(1-methyl-4-pyridiniothiomethyl)-3-cephem-4-carboxylate (syn isomer), mp. 160° to 165° C. (dec.).

I.R. (Nujol): 3300, 1765, 1670, 1630, 1600, 1525, 1495 cm$^{-1}$.

N.M.R. ($D_2O$, δ): 1.33 (3H, t, J=7 Hz), 3.45 and 3.70 (2H, ABq, J=17 Hz), 4.17 (3H, s), 4.32 (2H, q, J=7 Hz), 4.0–4.55 (2H, m), 5.15 (1H, d, J=5 Hz), 5.78 (1H, d, J=5 Hz), 7.70 (2H, d, J=7 Hz), 8.30 (2H, d, J=7 Hz).

(2) 7-[2-Carboxymethoxyimino-2-(5-amino-1,2,4-thiadiaziol-3-yl)acetamido]-3-(1-methyl-2-pyridiniothiomethyl)-3-cephem-4-carboxylate (syn isomer), mp. 145° to 150° C. (dec.).

I.R. (Nujol): 3290, 3180, 1765, 1675, 1615, 1560, 1530, 1490 cm$^{-1}$.

N.M.R. ($CD_3OD$+$D_2O$+DCl, δ): 3.80 (2H, broad s), 4.33 (3H, s), 4.32 and 4.60 (2H, Abq, J=14 Hz), 4.92 (2H, s), 5.27 (1H, d, J=5 Hz), 5.87 (1H, d, J=5 Hz), 7.50–8.90 (4H, m).

(3) 7-[2-Ethoxyimino-2-(5-amino-1,2,4-thiadiazol-3-yl)acetamido]-3-(1-carboxymethyl-2-pyridiniothiomethyl)-3-cephem-4-carboxylate (syn isomer), mp. 150° to 155° C. (dec.).

IR (Nujol): 3300, 3180, 1770, 1665, 1610, 1560, 1525, 1485 cm$^{-1}$.

NMR ($CD_3OD$+$D_2O$, δ): 1.32 (3H, t, J=7 Hz), 3.67 (2H, broad s), 4.30 (2H, q, J=7 Hz), 4.43 (2H, broad s), 5.15 (1H, d, J=5 Hz), 5.27 (2H, s), 5.82 (1H, d, J=5 Hz), 7.40–8.83 (4H, m).

(4) 7-[2-Ethoxyimino-2-(5-amino-1,2,4-thiadiazol-3-yl)acetamido]-3-(1-carbamoylmethyl-2-pyridiniothiomethyl)-3-cephem-4-carboxylate (syn isomer), mp. 130° to 135° C. (dec.).

IR (Nujol): 3400, 3300, 3170, 1770, 1690, 1670, 1610, 1560, 1525, 1485 cm$^{-1}$.

NMR ($CD_3COCD_3$+$D_2O$, δ): 1.32 (3H, t, J=7 Hz), 3.54 and 3.72 (2H, ABq, J=18 Hz), 4.0–4.6 (4H, m), 5.18 (1H, d, J=5 Hz), 5.58 (2H, s), 5.82 (1H, d, J=5 Hz), 7.76–7.96 (1H, m), 8.04–8.24 (1H, m), 8.32–8.56 (1H, m), 8.68–8.88 (1H, m).

(5) 7-[2-Ethoxyimino-2-(5-amino-1,2,4-thiadiazol-3-yl)acetamido]-3-[1-(2-hydroxyethyl)-2-pyridiniothiomethyl]-3-cephem-4-carboxylate (syn isomer), mp. 130° to 135° C. (dec.).

IR (Nujol): 3250, 3160, 1765, 1670, 1610, 1560, 1530, 1490 cm$^{-1}$.

NMR ($D_2O$+$CD_3OD$, δ): 1.33 (3H, t, J=7 Hz), 3.52 and 3.73 (2H, ABq, J=18 Hz), 3.97–4.17 (2H, m), 4.33 (2H, q, J=7 Hz), 4.33–5.00 (4H, m), 5.15 (1H, d, J=5 Hz), 5.80 (1H, d, J=5 Hz), 7.40–8.83 (4H, m).

(6) 7-[2-Ethoxyimino-2-(5-amino-1,2,4-thiadiazol-3-yl)acetamido]-3-(1-methyl-3-amino-2-pyridiniothiomethyl)-3-cephem-4-carboxylate (syn isomer), mp. 150° to 155° C. (dec.).

IR (Nujol): 3300, 1760, 1660, 1620 cm$^{-1}$.

NMR ($D_2O$+DCl+$CD_3OD$, δ): 1.30 (3H, t, J=7 Hz), 3.82 (2H, broad s), 4.30 (2H, q, J=7 Hz), 4.33 (3H, s), 4.0–4.5 (2H, m), 5.18 (1H, d, J=4 Hz), 5.80 (1H, d, J=4 Hz), 7.5–7.8 (2H, m), 8.0–8.3 (1H, m).

(7) 7-[2-Ethoxyimino-2-(5-amino-1,2,4-thiadiazol-3-yl)acetamido]-3-[1-(2-hydroxyethyl)-2,6-dimethyl-4-pyridiniothiomethyl]-3-cephem-4-carboxylate (syn isomer), mp. 187° to 191° C. (dec.).

IR (Nujol): 3250, 3150, 1760, 1670, 1620, 1550, 1520 cm$^{-1}$.

NMR ($D_2O$+$CD_3OD$, δ): 1.32 (3H, t, J=7 Hz), 2.78 (6H, s), 3.37 and 3.77 (2H, ABq, J=18 Hz), 3.98 (2H, t, J=5 Hz), 4.33 (2H, q, J=7 Hz), 4.33–4.88 (4H, m), 5.13 (1H, d, J=5 Hz), 5.80 (1H, d, J=5 Hz), 7.62 (2H, s).

(8) 7-[2-Ethoxyimino-2-(5-amino-1,2,4-thiadiazol-3-yl)acetamido]-3-[1-(2-t-butoxycarbonylaminoethyl)-2,6-dimethyl-4-pyridiniothiomethyl]-3-cephem-4-carboxylate (syn isomer), mp. 160°–165° C. (dec.).

IR (Nujol): 3350–3200, 1760, 1680, 1620, 1520 cm$^{-1}$.

NMR ($D_2O$+$CD_3OD$, δ): 1.30 (9H, s), 1.33 (3H, t, J=7 Hz), 2.80 (6H, s), 3.4–3.9 (4H, m), 4.37 (2H, q, J=7 Hz), 4.37–4.80 (4H, m), 5.15 (1H, d, J=5 Hz), 5.80 (1H, d, J=5 Hz), 7.98 (2H, s).

(9) 7-[2-Ethoxyimino-2-(5-amino-1,2,4-thiadiazol-3-yl)acetamido]-3-(1-carboxymethyl-2,6-dimethyl-4-pyridiniothiomethyl)-3-cephem-4-carboxylate (syn isomer), mp. 180° to 185° C. (dec.).

IR (Nujol): 3300, 3150, 1770, 1670, 1620, 1550, 1520 cm$^{-1}$.

NMR ($D_2O$+$CD_3OD$, δ): 1.32 (3H, t, J=7 Hz), 2.60 (6H, s), 3.48 and 3.74 (2H, ABq, J=18 Hz), 4.32 (2H, q, J=7 Hz), 4.38–4.80 (2H, m), 4.96 (2H, s), 5.16 (1H, d, J=5 Hz), 5.80 (1H, d, J=5 Hz), 7.58 (2H, s).

(10) 7-[2-Ethoxyimino-2-(5-amino-1,2,4-thiadiazol-3-yl)acetamido]-3-[1-(2-aminoethyl)-2,6-dimethyl-4-pyridiniothiomethyl]-3-cephem-4-carboxylate (syn isomer), mp. 200° to 205° C. (dec.).

IR (Nujol): 3300, 3200, 3150, 1760, 1660, 1610, 1590, 1550 cm$^{-1}$.

(11) 7-[2-Ethoxyimino-2-(5-amino-1,2,4-thiadiazol-3-yl)acetamido]-3-[1-(2-hydroxyethyl)-4-pyridiniothiomethyl]-3-cephem-4-carboxylate (syn isomer), mp. 165° to 170° C. (dec.).

IR (Nujol): 3280, 3170, 3130, 1765, 1670, 1630, 1595, 1545, 1525, 1490 cm$^{-1}$.

NMR ($D_2O$, δ): 1.33 (3H, t, J=7 Hz), 3.48 and 3.72 (2H, ABq, J=18 Hz), 4.33 (2H, q, J=7 Hz), 3.9–4.9 (6H, m), 5.18 (1H, d, J=5 Hz), 5.80 (1H, d, J=5 Hz), 7.80 (2H, d, J=7 Hz), 8.43 (2H, d, J=7 Hz).

EXAMPLE 4

A solution of 7-[2-ethoxyimino-2-(5-amino-1,2,4-thiadiazol-3-yl)acetamido]-3-[1-(2-t-butoxycarbonylaminoethyl)-2,6-dimethyl-4-pyridiniothiomethyl]-3-cephem-4-carboxylate (syn isomer) (1.91 g) in formic acid (20 ml) was stirred for 4 hours at room temperature and evaporated to dryness under reduced pressure. The residue was triturated in diethyl ether and filtered. The powder was dissolved in water (20 ml) and subjected to column chromatography on a non ionic adsorption resin "Diaion HP-20" (60 ml). After the column was washed with water, the elution was carried out with 20% aqueous methanol. The eluate was evaporated to remove methanol under reduced pressure and lyophilized to give 7-[2-ethoxyimino-2-(5-amino-1,2,4-thiadiazol-3-yl)acetamido]-3-[1-(2-aminoethyl)-2,6-dimethyl-4-pyridiniothiomethyl]-3-cephem-4-carboxylate (syn isomer) (0.60 g), mp. 200° to 205° C. (dec.).

IR (Nujol): 3300, 3200, 3150, 1760, 1660, 1610, 1590, 1550 cm$^{-1}$.

NMR ($D_2O+CD_3OD$, δ): 1.33 (3H, t, J=7 Hz), 2.77 (6H, s), 3.33–3.70 (4H, m), 4.30 (2H, q, J=7 Hz), 4.30–4.87 (4H, m), 5.12 (1H, d, J=5 Hz), 5.77 (1H, d, J=5 Hz), 7.60 (2H, s).

EXAMPLE 5

A solution of crude 7-amino-3-(1-methyl-4-pyridiniothiomethyl)-3-cephem-4-carboxylate (463 mg) in 50% aqueous acetone (10 ml) was adjusted to pH 6.0 with an aqueous solution of sodium bicarbonate under cooling in an ice bath and 2-carboxymethoxyimino-2-(5-amino-1,2,4-thiadiazol-3-yl)acetic methanesulfonic anhydride (syn isomer) (324 mg) was added thereto. The mixture was adjusted to pH 6.0 with an aqueous solution of sodium bicarbonate under cooling in an ice bath and stirring, which was continued for 20 minutes. The reaction mixture was adjusted to pH 3.0 with 1N hydrochloric acid and the resulting precipitates were collected by filtration to give 7-[2-carboxymethoxyimino-2-(5-amino-1,2,4-thiadiazol-3-yl)acetamido]-3-(1-methyl-4-pyridiniothiomethyl)-3-cephem-4-carboxylate (syn isomer) (200 mg). The filtrate was concentrated to remove acetone and adjusted to pH 2 with 1N hydrochloric acid. The resulting precipitates were collected, washed with water and dried to give the further crops (200 mg) of the object compound.

NMR ($D_2O+Na_dHCO_3$, δ): 3.56 and 3.80 (2H, ABq, J=18 Hz), 4.30 (3H, s), 4.30 and 5.44 (2H, ABq, J=14 Hz), 5.32 (1H, d, J=4 Hz), 5.96 (1H, d, J=4 Hz), 7.90 (2H, d, J=7 Hz), 8.42 (2H, d, J=7 Hz).

EXAMPLE 6

A solution of crude 7-amino-3-(1-methyl-4-pyridiniothiomethyl)-3-cephem-4-carboxylate (5.0 g) in 50% aqueous acetone (100 ml) was adjusted to pH 6.5 with triethylamine under cooling in an ice bath. To the solution was added 2-cyclopentyloxyimino-2-(5-amino-1,2,4-thiadiazol-3-yl)acetyl chloride hydrochloride (syn isomer) (4.37 g) by portions keeping pH 6.0 to 7.5 with triethylamine under cooling in an ice bath and stirring during the addition. After the addition, the mixture was stirred for 30 minutes at 5° to 6° C. and evaporated to remove acetone under reduced pressure. The aqueous solution was diluted to 300 ml with water and adjusted to pH 3.0 with 1N hydrochloric acid. After an insoluble material was filtered off, the filtrate was subjected to column chromatography on a non ionic adsorption resin Diaion HP-20 (125 ml). After the column was washed with water, the elution was carried out with 50% aqueous methanol. The eluates containing an object compound were collected and concentrated to 40 ml under reduced pressure. The resulting precipitates were collected, washed with water and crystallized from 50% aqueous N,N-dimethylformamide to give 7-[2-cyclopentyloxyimino-2-(5-amino-1,2,4-thiadiazol-3-yl)acetamido]-3-(1-methyl-4-pyridiniothiomethyl)-3-cephem-4-carboxylate (syn isomer) (2.04 g).

mp. 165° to 168° C. (dec.).

IR (Nujol): 3300, 3100, 1780, 1650, 1630, 1590, 1530, 1515, 1495 cm$^{-1}$.

NMR ($DMSO-d_6+D_2O$, δ): 1.70 (8H, broad s), 3.40 (2H, m), 4.10 (3H, s), 4.40 (2H, m), 4.70 (1H, m), 4.97 (1H, d, J=5 Hz), 5.57 (1H, d, J=5 Hz), 8.00 (2H, d, J=7 Hz), 8.50 (2H, d, J=7 Hz).

EXAMPLE 7

The following compounds were obtained according to similar manners to those of Examples 5 and 6.

(1) 7-[2-Ethoxyimino-2-(5-amino-1,2,4-thiadiazol-3-yl)acetamido]-3-(1-methyl-2-pyridiniothiomethyl)-3-cephem-4-carboxylate (syn isomer), mp. 125° to 130° C. (dec.).

IR (Nujol): 3280, 3150, 1760, 1665, 1610, 1560, 1530, 1490 cm$^{-1}$.

(2) 7-[2-Carboxymethoxyimino-2-(5-amino-1,2,4-thiadiazol-3-yl)acetamido]-3-(1-methyl-4-pyridiniothiomethyl)-3-cephem-4-carboxylate (syn isomer), mp. 155° to 160° C. (dec.).

IR (Nujol): 3290, 3180, 1765, 1670, 1630, 1600, 1550, 1520, 1495 cm$^{-1}$.

(3) 7-[2-Ethoxyimino-2-(5-amino-1,2,4-thiadiazol-3-yl)acetamido]-3-(1-methyl-4-pyridiniothiomethyl)-3-cephem-4-carboxylate (syn isomer), mp. 160° to 165° C. (dec.).

IR (Nujol): 3300, 1765, 1670, 1630, 1600, 1525, 1495 cm$^{-1}$.

(4) 7-[2-Carboxymethoxyimino-2-(5-amino-1,2,4-thiadiazol-3-yl)acetamido]-3-(1-methyl-2-pyridiniothiomethyl)-3-cephem-4-carboxylate (syn isomer), mp. 145° to 150° C. (dec.).

IR (Nujol): 3290, 3180, 1765, 1675, 1615, 1560, 1530, 1490 cm$^{-1}$.

(5) 7-[2-Ethoxyimino-2-(5-amino-1,2,4-thiadiazol-3-yl)acetamido]-3-(1-carboxymethyl-2-pyridiniothiomethyl)-3-cephem-4-carboxylate (syn isomer), mp. 150° to 155° C. (dec.).

IR (Nujol): 3300, 3180, 1770, 1665, 1610, 1560, 1525, 1485 cm$^{-1}$.

(6) 7-[2-Ethoxyimino-2-(5-amino-1,2,4-thiadiazol-3-yl)acetamido]-3-(1-carbamoylmethyl-2-pyridiniothiomethyl)-3-cephem-4-carboxylate (syn isomer), mp. 130° to 135° C. (dec.).

IR (Nujol): 3400, 3300, 3170, 1770, 1690, 1670, 1610, 1560, 1525, 1485 cm$^{-1}$.

(7) 7-[2-Ethoxyimino-2-(5-amino-1,2,4-thiadiazol-3-yl)acetamido]-3-[1-(2-hydroxyethyl)-2-pyridiniothiomethyl]-3-cephem-4-carboxylate (syn isomer), mp. 130° to 135° C. (dec.).

IR (Nujol): 3250, 3160, 1765, 1670, 1610, 1560, 1530, 1490 cm$^{-1}$.

(8) 7-[2-Ethoxyimino-2-(5-amino-1,2,4-thiadiazol-3-yl)acetamido]-3-(1-methyl-3-amino-2-pyridiniothiomethyl)-3-cephem-4-carboxylate (syn isomer), mp. 150° to 155° C. (dec.).

IR (Nujol): 3300, 1760, 1660, 1620 cm$^{-1}$.

(9) 7-[2-Ethoxyimino-2-(5-amino-1,2,4-thiadiazol-3-yl)acetamido]-3-[1-(2-hydroxyethyl)-2,6-dimethyl-4-pyridiniothiomethyl]-3-cephem-4-carboxylate (syn isomer), mp. 187° to 191° C. (dec.).

IR (Nujol): 3250, 3150, 1760, 1670, 1620, 1550, 1520 cm$^{-1}$.

(10) 7-[2-Ethoxyimino-2-(5-amino-1,2,4-thiadiazol-3-yl)acetamido]-3-[1-(2-t-butoxycarbonylaminoethyl)-2,6-dimethyl-4-pyridiniothiomethyl]-3-cephem-4-carboxylate (syn isomer), mp. 160°-165° C. (dec.).

IR (Nujol): 3350-3200, 1760, 1680, 1620, 1520 cm$^{-1}$.

(11) 7-[2-Ethoxyimino-2-(5-amino-1,2,4-thiadiazol-3-yl)acetamido]-3-(1-carboxymethyl-2,6-dimethyl-4-pyridiniothiomethyl)-3-cephem-4-carboxylate (syn isomer), mp. 180° to 185° C. (dec.).

IR (Nujol): 3300, 3150, 1770, 1670, 1620, 1550, 1520 cm$^{-1}$.

(12) 7-[2-Ethoxyimino-2-(5-amino-1,2,4-thiadiazol-3-yl)acetamido]-3-[1-(2-aminoethyl)-2,6-dimethyl-4-pyridiniothiomethyl]-3-cephem-4-carboxylate (syn isomer), mp. 200° to 205° C. (dec.).

IR (Nujol): 3300, 3200, 3150, 1760, 1660, 1610, 1590, 1550 cm$^{-1}$.

(13) 7-[2-Ethoxyimino-2-(5-amino-1,2,4-thiadiazol-3-yl)acetamido]-3-[1-(2-hydroxyethyl)-4-pyridiniothiomethyl]-3-cephem-4-carboxylate (syn isomer), mp. 165° to 170° C. (dec.).

IR (Nujol): 3280, 3170, 3130, 1765, 1670, 1630, 1595, 1545, 1525, 1490 cm$^{-1}$.

(14) 7-[2-(2-Propynyloxyimino)-2-(5-amino-1,2,4-thiadiazol-3-yl)acetamido]-3-(1-methyl-4-pyridiniothiomethyl)-3-cephem-4-carboxylate (syn isomer), mp. 135° to 143° C. (dec.).

IR (Nujol): 3250, 2080, 1760, 1670, 1630, 1600, 1550, 1530, 1490 cm$^{-1}$.

NMR (D$_6$-acetone+D$_2$O, δ): 3.07 (1H, t, J=2 Hz), 3.48 and 3.77 (2H, ABq, J=18 Hz), 4.27 (3H, s), 4.27 and 4.53 (2H, ABq, J=14 Hz), 4.95 (2H, d, J=2 Hz), 5.22 (1H, d, J=5 Hz), 5.86 (1H, d, J=5 Hz), 7.90 (2H, d, J=7 Hz), 8.50 (2H, d, J=7 Hz).

(15) 7-[2-Allyloxyimino-2-(5-amino-1,2,4-thiadiazol-3-yl)acetamido]-3-(1-methyl-4-pyridiniothiomethyl)-3-cephem-4-carboxylate (syn isomer), mp. 149° to 156° C. (dec.).

IR (Nujol): 3250, 1760, 1670, 1630, 1600, 1520 cm$^{-1}$.

(16) 7-[2-(2-Cyclopenten-1-yloxyimino)-2-(5-amino-1,2,4-thiadiazol-3-yl)acetamido]-3-(1-methyl-4-pyridiniothiomethyl)-3-cephem-4-carboxylate (syn isomer), mp. 170° to 175° C. (dec.).

IR (Nujol): 3300, 1780, 1640, 1630, 1600, 1520, 1490 cm$^{-1}$.

(17) 7-[2-Methylthiomethoxyimino-2-(5-amino-1,2,4-thiadiazol-3-yl)acetamido]-3-(1-methyl-4-pyridiniothiomethyl)-3-cephem-4-carboxylate (syn isomer), mp. 165° to 168° C. (dec.).

IR (Nujol): 3100-2650, 1760, 1670, 1630, 1600, 1550, 1520, 1490 cm$^{-1}$.

(18) 7-[2-Methoxyimino-2-(5-amino-1,2,4-thiadiazol-3-yl)acetamido]-3-(1-methyl-4-pyridiniothiomethyl)-3-cephem-4-carboxylate (syn isomer), mp. 150° to 155° C. (dec.).

IR (Nujol): 3280, 3160, 3110, 3020, 1765, 1670, 1630, 1600, 1550, 1525, 1495 cm$^{-1}$.

(19) 7-[2-(1-t-Butoxycarbonyl-1-methylethoxyimino)-2-(5-amino-1,2,4-thiadiazol-3-yl)acetamido]-3-(1-methyl-4-pyridiniothiomethyl)-3-cephem-4-carboxylate (syn isomer), mp. 150° to 155° C. (dec.).

IR (Nujol): 3270, 3150, 3100, 1765, 1720, 1670, 1630, 1600, 1520, 1495, 1200, 1140, 1105 cm$^{-1}$.

NMR (DMSO-d$_6$+D$_2$O, δ): 1.41 (9H, s), 1.47 (6H, s), 3.50 (2H, broad s), 4.18 (3H, s), 4.52 (2H, broad s), 5.08 (1H, d, J=5 Hz), 5.68 (1H, d, J=5 Hz), 8.22 (2H, d, J=7 Hz), 8.67 (2H, d, J=7 Hz).

(20) 7-[2-(1-Carboxy-1-methylethoxyimino)-2-(5-amino-1,2,4-thiadiazol-3-yl)acetamido]-3-(1-methyl-4-pyridiniothiomethyl)-3-cephem-4-carboxylate (syn isomer), mp. 180° to 185° C. (dec.).

IR (Nujol): 3300, 3170, 3100, 1770, 1670, 1630, 1525, 1280, 1170, 1110 cm$^{-1}$.

(21) 7-[2-Trityloxyimino-2-(5-amino-1,2,4-thiadiazol-3-yl)acetamido]-3-(1-methyl-4-pyridiniothiomethyl)-3-cephem-4-carboxylate (syn isomer), mp. 180° to 185° C. (dec.).

IR (Nujol): 1755, 1680, 1630, 1620, 1530 cm$^{-1}$.

NMR (DMSO-d$_6$, δ): 3.32 and 3.56 (2H, ABq, J=17 Hz), 4.12 (3H, s), 4.3-4.8 (2H, m), 5.05 (1H, d, J=5 Hz), 5.80 (1H, dd, J=5 and 8 Hz), 7.22 (15H, s), 7.8-8.3 (4H, m), 8.4-8.8 (2H, m), 9.68 (1H, d, J=8 Hz).

(22) 7-[2-Hydroxyimino-2-(5-amino-1,2,4-thiadiazol-3-yl)acetamido]-3-(1-methyl-4-pyridiniothiomethyl)-3-cephem-4-carboxylate (syn isomer), mp. 184° to 188° C. (dec.).

IR (Nujol): 1770, 1670, 1635, 1530, 1500 cm$^{-1}$.

EXAMPLE 8

A mixture of sodium 7-[2-methoxyimino-2-(5-amino-1,2,4-thiadiazol-3-yl)acetamido]cephalosporanate (syn isomer) (2.9 g), 1-methylpyrid-4-thione (910 mg), sodium iodide (9 g), and water (3 ml) was stirred for 2.5 hours at 60° to 65° C. The mixture was diluted with water (100 ml) and ethyl acetate (100 ml) and then adjusted to pH 2.8 with 6N hydrochloric acid. The aqueous layer was separated out, washed with ethyl acetate and evaporated to remove ethyl acetate under reduced pressure. The aqueous solution was subjected to column chromatography on a non ionic adsorption resin Diaion HP-20 (100 ml). After the column was washed with water, the elution was carried out with 30% aqueous methanol. The eluates containing an object compound were collected, evaporated to remove methanol under reduced pressure and lyophilized to give 7-[2-methoxyimino-2-(5-amino-1,2,4-thiadiazol-3-yl)-acetamido]-3-(1-methyl-4-pyridiniothiomethyl)-3-cephem-4-carboxylate (syn isomer) (1.5 g), mp. 150° to 155° C. (dec.).

IR (Nujol): 3280, 3160, 3110, 3020, 1765, 1670, 1630, 1600, 1550, 1525, 1495 cm$^{-1}$.

NMR (CD$_3$OD+D$_2$O, δ): 3.43 and 3.73 (2H, ABq, J=18 Hz), 4.07 (3H, s), 4.20 (3H, s), 4.23 and 4.47 (2H, ABq, J=14 Hz), 5.15 (1H, d, J=5 Hz), 5.80 (1H, d, J=5 Hz), 7.85 (2H, d, J=7 Hz), 8.43 (2H, d, J=7 Hz).

EXAMPLE 9

The following compounds were obtained according to similar manners to those of Examples 1,2 and 8.

(1) 7-[2-(2-Propynyloxyimino)-2-(5-amino-1,2,4-thiadiazol-3-yl)acetamido]-3-(1-methyl-4-pyridiniothiomethyl)-3-cephem-4-carboxylate (syn isomer), mp. 135° to 143° C. (dec.).

IR (Nujol): 3250, 2080, 1760, 1670, 1630, 1600, 1550, 1530, 1490 cm$^{-1}$.

(2) 7-[2-Allyloxyimino-2-(5-amino-1,2,4-thiadiazol-3-yl)acetamido]-3-(1-methyl-4-pyridiniothiomethyl)-3-cephem-4-carboxylate (syn isomer), mp. 149° to 156° C. (dec.).

IR (Nujol): 3250, 1760, 1670, 1630, 1600, 1520 cm$^{-1}$.

NMR (D$_6$-acetone+D$_2$O, δ): 3.50 and 3.80 (2H, ABq, J=18 Hz), 4.30 (3H, s), 4.36 and 4.57 (2H, ABq, J=14 Hz), 4.87 (2H, m), 5.23 (1H, d, J=5 Hz), 5.2-5.7

(2H, m), 5.94 (1H, d, J=5 Hz), 5.75-6.35 (1H, m), 8.05 (2H, d, J=7 Hz), 8.65 (2H, d, J=7 Hz).

(3) 7-[2-(2-Cyclopenten-1-yloxyimino)-2-(5-amino-1,2,4-thiadiazol-3-yl)acetamido]-3-(1-methyl-4-pyridiniothiomethyl)-3-cephem-4-carboxylate (syn isomer), mp. 170° to 175° C. (dec.).

IR (Nujol): 3300, 1780, 1640, 1630, 1600, 1520, 1490 cm$^{-1}$.

NMR (DMSO-d$_6$, δ): 1.9-2.5 (4H, m), 3.47 (2H, broad s), 4.17 (3H, s), 4.50 (2H, broad s), 5.00 (1H, d, J=4 Hz), 5.23-5.50 (1H, m), 5.62 (1H, 2d, J=4 and 8 Hz), 5.83-6.23 (2H, m), 8.23 (2H, d, J=7 Hz), 8.27 (2H, s), 8.67 (2H, d, J=7 Hz), 9.40 (1H, d, J=8 Hz).

(4) 7-[2-Methylthiomethoxyimino-2-(5-amino-1,2,4-thiadiazol-3-yl)acetamido]-3-(1-methyl-4-pyridiniothiomethyl)-3-cephem-4-carboxylate (syn isomer), mp. 165° to 168° C. (dec.).

IR (Nujol): 3100-2650, 1760, 1670, 1630, 1600, 1550, 1520, 1490 cm$^{-1}$.

NMR (DMSO-d$_6$+D$_2$O, δ): 2.20 (3H, s), 3.47 (2H, broad s), 4.15 (3H, s), 4.45 (2H, broad s), 5.00 (1H, d, J=5 Hz), 5.27 (2H, s), 5.65 (1H, d, J=5 Hz), 8.07 (2H, d, J=7 Hz), 8.55 (2H, d, J=7 Hz).

(5) 7-[2-Cyclopentyloxyimino-2-(5-amino-1,2,4-thiadiazol-3-yl)acetamido]-3-(1-methyl-4-pyridiniothiomethyl)-3-cephem-4-carboxylate (syn isomer), mp. 165° to 168° C. (dec.).

IR (Nujol): 3300, 3100, 1780, 1650, 1630, 1590, 1530, 1515, 1495 cm$^{-1}$.

(6) 7-[2-(1-t-Butoxycarbonyl-1-methylethoxyimino)-2-(5-amino-1,2,4-thiadiazol-3-yl)acetamido]-3-(1-methyl-4-pyridiniothiomethyl)-3-cephem-4-carboxylate (syn isomer), mp. 150° to 155° C. (dec.).

IR (Nujol): 3270, 3150, 3100, 1765, 1720, 1670, 1630, 1600, 1520, 1495, 1200, 1140, 1105 cm$^{-1}$.

(7) 7-[2-(1-Carboxy-1-methylethoxyimino)-2-(5-amino-1,2,4-thiadiazol-3-yl)acetamido]-3-(1-methyl-4-pyridiniothiomethyl)-3-cephem-4-carboxylate (syn isomer), mp. 180° to 185° C. (dec.).

IR (Nujol): 3300, 3170, 3100, 1770, 1670, 1630, 1525, 1280, 1170, 1110 cm$^{-1}$.

(8) 7-[2-Trityloxyimino-2-(5-amino-1,2,4-thiadiazol-3-yl)acetamido]-3-(1-methyl-4-pyridiniothiomethyl)-3-cephem-4-carboxylate (syn isomer), mp. 180° to 185° C. (dec.).

IR (Nujol): 1755, 1680, 1630, 1620, 1530 cm$^{-1}$.

(9) 7-[2-Hydroxyimino-2-(5-amino-1,2,4-thiadiazol-3-yl)acetamido]-3-(1-methyl-4-pyridiniothiomethyl)-3-cephem-4-carboxylate (syn isomer), mp. 184° to 188° C. (dec.).

IR (Nujol): 1770, 1670, 1635, 1530, 1500 cm$^{-1}$.

EXAMPLE 10

A mixture of 7-[2-(1-t-butoxycarbonyl-1-methylethoxyimino)-2-(5-amino-1,2,4-thiadiazol-3-yl)acetamido]-3-(1-methyl-4-pyridiniothiomethyl)-3-cephem-4-carboxylate (syn isomer) (2.29 g) and anisole (2.65 ml) in trifluoroacetic acid (16 ml) was stirred for one hour at room temperature. The reaction mixture was evaporated under reduced pressure and the residue was triturated in diisopropyl ether, filtered and washed with the same solvent. The precipitate was dissolved in water (100 ml) at 35° to 40° C. and an insoluble material was filtered off. The filtrate was subjected to column chromatography on a non ionic adsorption resin Diaion HP-20 (100 ml). After the column was washed with water, the elution was carried out with 30% aqueous methanol (500 ml). The eluate was evaporated to remove methanol under reduced pressure and lyophilized to give 7-[2-(1-carboxy-1-methylethoxyimino)-2-(5-amino-1,2,4-thiadiazol-3-yl)acetamido]-3-(1-methyl-4-pyridiniothiomethyl)-3-cephem-4-carboxylate (syn isomer) (970 mg), mp. 180° to 185° C. (dec.).

IR (Nujol): 3300, 3170, 3100, 1770, 1670, 1630, 1630, 1525, 1280, 1170, 1110 cm$^{-1}$.

NMR (DCl+D$_2$O, δ): 1.65 (6H, s), 3.77 (2H, broad s), 4.25 (3H, s), 4.47 (2H, broad s), 5.33 (1H, d, J=5 Hz), 5.87 (1H, d, J=5 Hz), 7.83 (2H, d, J=7 Hz), 8.48 (2H, d, J=7 Hz).

EXAMPLE 11

The following compounds were obtained according to a similar manner to that of Example 10.

(1) 7-[2-Carboxymethoxyimino-2-(5-amino-1,2,4-thiadiazol-3-yl)acetamido]-3-(1-methyl-4-pyridiniothiomethyl)-3-cephem-4-carboxylate (syn isomer), mp. 155° to 160° C. (dec.).

IR (Nujol): 3290, 3180, 1765, 1670, 1630, 1600, 1550, 1520, 1495 cm$^{-1}$.

(2) 7-[2-Carboxymethoxyimino-2-(5-amino-1,2,4-thiadiazol-3-yl)acetamido]-3-(1-methyl-2-pyridiniothiomethyl)-3-cephem-4-carboxylate (syn isomer), mp. 145° to 150° C. (dec.).

IR (Nujol): 3290, 3180, 1765, 1675, 1615, 1560, 1530, 1490 cm$^{-1}$.

Preparation 12

A mixture of sodium salt (45 g) of 2-hydroxyiminopropanedinitrile, methyl chloroacetate (41.8 g) and sodium iodide (5.8 g) in acetonitrile (225 ml) was stirred for 3 hours at 50° C. and allowed to stand overnight at room temperature. The reaction mixture was evaporated and the residue was dissolved in a mixture of diisopropyl ether and water. The organic layer was separated out, washed with water, dried over magnesium sulfate and evaporated to give crude oil (45.0 g) of 2-methoxycarbonylmethoxyiminopropanedinitrile, which was purified by distillation, bp. 90° to 99° C. at 5.5 mmHg.

IR (Film): 3050, 3000, 2250, 1765 cm$^{-1}$.

Preparation 13

To a solution of ammonium acetate (4.62 g) in methanol (10 ml) was added 2-methoxycarbonylmethoxyiminopropanedinitrile (3.34 g) under stirring, which was continued for 2 hours at room temperature and allowed to stand overnight. To the reaction mixture was added isopropyl alcohol (15 ml) and stirred for 15 minutes. The resulting precipitate was collected by filtration, washed with isopropyl alcohol and dried to give 2-cyano-2-methoxycarbonylmethoxyiminoacetamidine acetate (3.4 g), which was recrystalized from methanol, mp. 157° to 158° C. (dec.).

IR (Nujol): 2800-2200, 1750, 1680, 1550 cm$^{-1}$

NMR (DMSO-d$_6$, δ): 1.90 (3H, s), 3.73 (3H, s), 5.10 (2H, s), 7.0-7.5 (4H, broad s).

Preparation 14

To a suspension of 2-cyano-2-methoxycarbonylmethoxyiminoacetamidine acetate (495 g) in methanol (4.95 l) was dropped triethylamine (512.6 g) at −10° C. under stirring and cooling, and further, bromine (357.3 g) was added to the above mixture at the same temperature. After the reaction mixture was stirred for 15 minutes, a solution of potassium thiocyanate (216 g) in methanol (2.16 l) was dropped thereto at −10° to −5°

C. under stirring, which was continued for 30 minutes at 0° to 5° C. The resulting precipitates were collected by filtration, washed with water (5 l) and dried to give 2-methoxycarbonylmethoxyimino-2-(5-amino-1,2,4-thiadiazol-3-yl)acetonitrile (syn isomer) (430 g), which was recrystallized from aqueous methanol, mp. 225° to 227° C. (dec.).

IR (Nujol): 3400, 3250, 3100, 1740, 1630, 1550 cm$^{-1}$.

NMR (DMSO-d$_6$, δ): 3.77 (3H, s), 5.17 (2H, s), 8.33 (2H, s).

Preparation 15

To a solution of sodium hydroxide (334.5 g) in water (8.36 l) was added 2-methoxycarbonylmethoxyimino-2-(5-amino-1,2,4-thiadiazol-3-yl)acetonitrile (syn isomer) (550 g) at room temperature and the mixture was stirred for 5 hours at 60° to 65° C. The reaction mixture was cooled in an ice bath, adjusted to pH 3.0 with 50% aqueous sulfuric acid and washed with ethyl acetate. The aqueous solution was salted out, adjusted to pH 1.0 with 50% aqueous sulfuric acid and extracted with acetonitrile (6×2.5 l) (extract A).

The combined extract A was dried over magnesium sulfate (10 kg) and filtered. To the filtrate was added a solution of sodium acetate (109 g) in methanol (1.2 l) under stirring, which was continued for 15 minutes. The resulting precipitates were collected by filtration, washed with acetonitrile and diisopropyl ether and dried to give sodium 2-carboxymethoxyimino-2-(5-amino-1,2,4-thiadiazol-3-yl)acetate (syn isomer) (342.8 g), mp. 155° to 160° C. (dec.).

IR (Nujol): 3320, 3180, 1720, 1630, 1530 cm$^{-1}$.

NMR (DMSO-d$_6$, δ): 4.48 (2H, s), 8.08 (2H, broad s).

The above obtained extract A was evaporated to dryness. The residue was recrystallized from methanol to give 2-carboxymethoxyimino-2-(5-amino-1,2,4-thiadiazol-3-yl)acetic acid (syn isomer), mp. 193° to 194° C. (dec.).

IR (Nujol): 3400, 3250, 3100, 2800–2200, 1730, 1630, 1540 cm$^{-1}$.

NMR (DMSO-d$_6$): 4.65 (2H, s), 8.15 (2H, s)

Analysis for C$_6$H$_6$N$_4$O$_5$S: Calcd: C 29.27, H 2.46, N 22.76, Found: C 29.18, H 2.58, N 22.09.

Preparation 16

To a solution of 2-carboxymethoxyimino-2-(5-amino-1,2,4-thiadiazol-3-yl)acetic acid (syn isomer) (45.0 g) in N,N-dimethylacetamide (432 ml) was added methanesulfonyl chloride (29.8 g) under stirring and cooling in an ice bath. The mixture was stirred for 25 minutes at 4° to 6° C. and finely powdered potassium hydrogen carbonate (48.4 g) was added thereto. The reaction mixture was stirred for 2.5 hours at 4° to 6° C. and then poured into a cold mixture of ethyl acetate (1.2 l), 1N hydrochloric acid (484 ml) and water (500 ml) below 10° C. under stirring. The organic layer was separated out and the aqueous phase was extracted with ethyl acetate (300 ml). The combined extracts were washed with cold water (800 ml) and a saturated aqueous solution of sodium chloride (800 ml), dried over magnesium sulfate and evaporated. The residue was triturated in methylene chloride (200 ml) to give 2-carboxymethoxyimino-2-(5-amino-1,2,4-thiadiazol-3-yl)acetic methanesulfonic anhydride (syn isomer) (28.0 g), mp. 143° to 146° C. (dec.).

IR (Nujol): 3410, 3280, 3100, 2750–2560, 1790, 1730, 1630, 1550, 1430 cm$^{-1}$.

Analysis for C$_7$H$_8$N$_4$O$_7$S$_2$: calc'd: C, 25.93, H, 2.49, N, 17.28, found: C 26.19 H 2.58 N 17.57.

Preparation 17

To a solution of 7-aminocephalosporanic acid (37.7 g) and boron trifluoride etherate (78.8 g) in acetonitrile (194 ml) was added 1-methylpyrid-4-thione at room temperature under stirring, which was continued for 43 hours at the same temperature. The reaction mixture was evaporated to dryness and the residue was dissolved in water (50 ml). An insoluble material was filtered off and the filtrate was poured into isopropyl alcohol (1 l) under stirring. The resulting precipitates were collected by filtration, washed with isopropyl alcohol and dried to give a crude object compound (52.0 g). The crude compound (2.0 g) was suspended in water (20 ml) and adjusted to pH 5.7 with an aqueous solution of sodium bicarbonate. The aqueous solution was subjected to column chromatography on a non ionic adsorption resin Diaion HP-20 (50 ml). After the column was washed with water, the elution was carried out with 15% aqueous methanol. The eluate was concentrated to 50 ml to remove methanol and lyophilized to give 7-amino-3-(1-methyl-4-pyridiniothiomethyl)-3-cephem-4-carboxylate (400 mg), mp. 145° to 150° C. (dec.).

IR (Nujol): 3300, 1750, 1630, 1600, 1550, 1490 cm$^{-1}$.

NMR (D$_2$O, δ): 3.47 and 3.67 (2H, ABq, J=18 Hz), 4.20 (3H, s), 4.20 and 4.43 (2H, ABq, J=14 Hz), 4.77 (1H, d, J=4 Hz), 5.00 (1H, d, J=4 Hz), 7.77 (2H, d, J=7 Hz), 8.43 (2H, d, J=7 Hz).

Preparation 18

To a solution of crude 7-amino-3-(1-methyl-4-pyridiniothiomethyl)-3-cephem-4-carboxylate (500 mg) in water (25 ml) was added sodium iodide (500 mg) and the mixture stirred for 30 minutes at room temperature. The resulting precipitates were collected by filtration, washed with cold water and dried to give 7-amino-3-(1-methyl-4-pyridiniothiomethyl)-3-cephem-4-carboxylate hydriodide (320 mg), mp. 175° to 180° C. (dec.).

IR (Nujol): 3400, 1800, 1630, 1550, 1490, 1110 cm$^{-1}$.

NMR (D$_2$O+DCl, δ): 3.87 (2H, s), 4.30 (3H, s), 4.67 (2H, s), 5.27 (1H, d, J=4 Hz), 5.47 (1H, d, J=4 Hz), 7.93 (2H, d, J=7 Hz), 8.57 (2H, d, J=7 Hz).

Preparation 19

To a mixture of 7-aminocephalosporanic acid (2.4 g) and boron trifluoride etherate (5.1 g) in trufluoroacetic acid (12 ml) was added crude 1-methylpyrid-4-thione (1.8 g, content 69.2%) at room temperature under stirring, which was continued for 5 hours at the same temperature. The mixture was evaporated and the residue was dissolved in water (6 ml). An insoluble material was filtered off and the filtrate was poured into isopropyl alcohol (80 ml) under stirring. The resulting precipitates were collected by filtration, washed with isopropyl alcohol and dried to give crude 7-amino-3-(1-methyl-4-pyridiniothiomethyl)-3-cephem-4-carboxylate (4.4 g), which contained 3.4 g of the pure one according to an identification by H P L C.

EXAMPLE 12

7-[2-Trityloxyimino-2-(5-amino-1,2,4-thiadiazol-3-yl)acetamido]-3-(1-methyl-4-pyridiniothiomethyl)-3-cephem-4-carboxylate (syn isomer) (1.5 g) was suspended in 15 ml of water. To the suspension was added 98% formic acid (15 ml) and the mixture was stirred for 50 minutes at ambient temperature to precipitate an insoluble material. The precipitates were filtered and washed with ethyl acetate (20 ml). The filtrate and the washings were combined and added to 400 ml of acetone, which was stirred for 10 minutes. Precipitates were collected by filtration, washed twice with dry acetone (30 ml) and dried to give 7-[2-hydroxyimino-2-(5-amino-1,2,4-thiadiazol-3-yl)-acetamido]-3-(1-methyl-4-pyridiniothiomethyl)-3-cephem-4-carboxylate (syn isomer) (630 mg), mp. 184° to 188° C. (dec.).

IR (Nujol): 1770, 1670, 1635, 1530, 1500 cm$^{-1}$.

NMR (DMSO-d$_6$+D$_2$O, δ): 3.2–3.7 (2H, m), 4.16 (3H, broad s), 4.4 (2H, m), 5.00 (1H, d, J=5 Hz), 5.65 (1H, d, J=5 Hz), 7.8–8.2 (2H, m), 7.4–7.8 (2H, m).

What we claim is:

1. New cephem compounds of the formula:

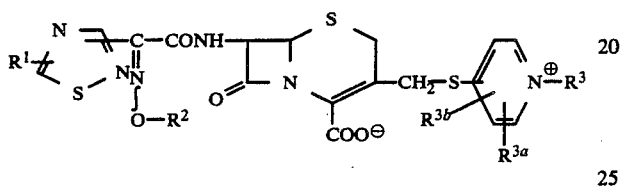

wherein
R$^1$ is amino or a protected amino group;
R$_2$ is hydrogen, lower aliphatic hydrocarbon group selected from lower alkyl, alkenyl and alkynyl which may be substituted with carboxy, protected carboxy, lower alkylthio or phenyl, cyclo(lower)alkyl, or cyclo(lower)alkenyl;
R$^3$ is lower alkyl which may be substituted with carboxy, carbamoyl, hydroxy, amino or protected amino;
R$^{3a}$ is hydrogen, lower alkyl or amino; and
R$^{3b}$ is hydrogen or lower alkyl; and
pharmaceutically acceptable salts thereof.

2. Syn isomer of a compound of claim 1, wherein

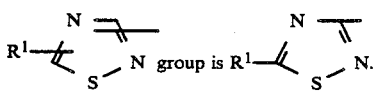

3. A compound of claim 2, wherein
R$^1$ is amino;
R$^2$ is hydrogen, lower aliphatic hydrocarbon group selected from lower alkyl, alkenyl and alkynyl which may be substituted with 1 to 3 carboxy, protected carboxy, lower alkylthio or phenyl, cyclo(lower)alkyl, or cyclo(lower)alkenyl; and
R$^3$ is lower alkyl which may be substituted with one carboxy, carbamoyl, hydroxy, amino or protected amino.

4. A compound of claim 3, wherein:
R$^2$ is hydrogen, lower alkyl which may be substituted with 1 to 3 carboxy, lower alkoxycarbonyl, lower alkylthio or phenyl, lower alkenyl, lower alkynyl, cyclo(lower)alkyl, or cyclo(lower)alkenyl and
R$^3$ is lower alkyl which may be substituted with one carboxy, carbamoyl, hydroxy, amino or lower alkoxycarbonylamino.

5. A compound of claim 4, wherein:
R$^2$ is hydrogen, R$^3$ is lower alkyl,
R$^{3a}$ is hydrogen and R$^{3b}$ is hydrogen.

6. A compound of claim 4, wherein:
R$^2$ is lower alkyl which may be substituted with 1 to 3 carboxy, lower alkoxycarbonyl, lower alkylthio or phenyl, lower alkenyl or lower alkynyl.

7. A compound of claim 6, wherein:
R$^2$ is lower alkyl substituted with one carboxy,
R$^3$ is lower alkyl, R$^{3a}$ is hydrogen and
R$^{3b}$ is hydrogen.

8. A compound of claim 7, which is:
7-[2-carboxymethoxyimino-2-(5-amino-1,2,4-thiadiazol-3-yl)acetamido]-3-(1-methyl-4-pyridiniothiomethyl)-3-cephem-4-carboxylate (syn isomer).

9. A compound of claim 4, wherein:
R$^2$ is cyclo(lower)alkyl or cyclo(lower)alkenyl,
R$^3$ is lower alkyl, R$^{3a}$ is hydrogen and R$^{3b}$ is hydrogen.

10. A compound of claim 4, wherein:
R$^2$ is hydrogen, methyl, ethyl, carboxymethyl, methylthiomethyl, 1-methyl-1-carboxyethyl, 1-methyl-1-t-butoxycarbonylethyl, trityl, allyl, 2-propynyl, cyclopentyl, or 2-cyclopenten-1-yl;
R$^3$ is methyl, carboxymethyl, carbamoylmethyl, 2-hydroxyethyl, 2-aminoethyl or 2-t-butoxycarbonylaminoethyl;
R$^{3a}$ is hydrogen, methyl or amino; and
R$^{3b}$ is hydrogen or methyl.

11. A compound of claim 10, which is selected from the compound consisting of:
7-[2-cyclopentyloxyimino-2-(5-amino-1,2,4-thiadiazol-3-yl)acetamido]-3-(1-methyl-4-pyridiniothiomethyl)-3-cephem-4-carboxylate (syn isomer),
7-[2-ethoxyimino-2-(5-amino-1,2,4-thiadiazol-3-yl)acetamido]-3-(1-methyl-2-pyridiniothiomethyl)-3-cephem-4-carboxylate (syn isomer),
7-[2-ethoxyimino-2-(5-amino-1,2,4-thiadiazol-3-yl)-acetamido]-3-(1-methyl-4-pyridiniothiomethyl)-3-cephem-4-carboxylate (syn isomer),
7-[2-carboxymethoxyimino-2-(5-amino-1,2,4-thiadiazol-3-yl)acetamido]-3-(1-methyl-2-pyridiniothiomethyl)-3-cephem-4-carboxylate (syn isomer),
7-[2-ethoxyimino-2-(5-amino-1,2,4-thiadiazol-3-yl)-acetamido]-3-(1-carboxymethyl-2-pyridiniothiomethyl)-3-cephem-4-carboxylate (syn isomer),
7-[2-ethoxyimino-2-(5-amino-1,2,4-thiadiazol-3-yl)-acetamido]-3-(1-carbamoylmethyl-2-pyridiniothiomethyl)-3-cephem-4-carboxylate (syn isomer),
7-[2-ethoxyimino-2-(5-amino-1,2,4-thiadiazol-3-yl)-acetamido]-3-[1-(2hydroxyethyl)-2-pyridiniothiomethyl]-3-cephem-4-carboxylate (syn isomer),
7-[2-ethoxyimino-2-(5-amino-1,2,4-thiadiazol-3-yl)acetamido]-3-(1-methyl-3-amino-2-pyridiniothiomethyl)-3-cephem-4-carboxylate (syn isomer),
7-[2-ethoxyimino-2-(5-amino-1,2,4-thiadiazol-3-yl)acetamido]-3-[1-(2-hydroxyethyl)-2,6-dimethyl-4-pyridiniothiomethyl]-3-cephem-4-carboxylate (syn isomer),
7-[2-ethoxyimino-2-(5-amino-1,2,4-thiadiazol-3-yl)acetamido]-3-(1-carboxymethyl-2,6-dimethyl-4-pyridiniothiomethyl)-3-cephem-4-carboxylate (syn isomer),
7-[2-ethoxyimino-2-(5-amino-1,2,4-thiadiazol-3-yl)acetamido]-3-[1-(2-aminoethyl)-2,6-dimethyl-4-pyridiniothiomethyl]-3-cephem-4-carboxylate (syn isomer), 7-[2-ethoxyimino-2-(5-amino-1,2,4-thiadiazol-3-yl)acetamido]-3-[1-(2-hydroxyethyl)-4-pyridiniothiomethyl]-3-cephem-4-carboxylate (syn isomer), 7-[2-(2-propynyloxyimino)-2-(5-amino-1,2,4-thiadiazol-3-yl)acetamido]-3-(1-methyl-4-pyridiniothiomethyl)-3-cephem-4-carboxylate (syn isomer), 7-[2-allyloxyimino-2-(5-amino-1,2,4-thiadiazol-3-yl)acetamido]-3-(1-methyl-4-pyridiniothiomethyl)-3-cephem-4-carboxylate (syn isomer), 7-[2-(2-cyclopenten-1-yloxyimino)-2-(5-amino 1,2,4-thiadiazol-3-yl)acetamido]-3-(1-methyl-4-pyridiniothiomethyl)-3-cephem-4-carboxylate (syn isomer), 7-[2-methylthiomethoxyimino-2-(5-amino-1,2,4-thiadiazol-3-yl)acetamido]-3-(1-methyl-4-pyridiniothiomethyl)-3-cephem-4-carboxylate (syn isomer), 7-[2-methoxyimino-2-(5-amino-1,2,4-thiadiazol-3-yl)acetamido]-3-(1-methyl-4-pyridiniothiomethyl)-3-cephem-4-carboxylate (syn isomer), 7-[2-(1-carboxy-1-methylethoxyimino)-2-(5-amino-1,2,4-thiadiazol-3-yl)acetamido]-3-(1-methyl-4-pyridiniothiomethyl)-3-cephem-4-carboxylate (syn isomer), and 7-[2-hydroxyimino-2-(5-amino-1,2,4-thiadiazol-3-yl)acetamido]-3-(1-methyl-4-pyridiniothiomethyl)-3-cephem-4-carboxylate (syn isomer).

12. A pharmaceutical antibacterial composition comprising an effective amount of a compound of claim 1 in association with a pharmaceutically acceptable, substantially non-toxic carrier or excipient.

13. A compound of claim 11 which is 7-[2-cyclopentyloxyimino-2-(5-amino-1,2,4-thiadiazol-3-yl)acetamido]-3-(1-methyl-4-pyridiniothiomethyl)-3-cephem-4-carboxylate (syn isomer).

14. A compound of claim 11 which is 7-[2-ethoxyimino-2-(5-amino-1,2,4-thiadiazol-3-yl)acetamido]-3-(1-methyl-2-pyridiniothiomethyl)-3-cephem-4-carboxylate (syn isomer).

15. A compound of claim 11 which is 7-[2-ethoxyimino-2-(5-amino-1,2,4-thiadiazol-3-yl)acetamido]-3-(1-methyl-4-pyridiniothiomethyl)-3-cephem-4-carboxylate (syn isomer).

16. A compound of claim 11 which is 7-[2-carboxymethoxyimino-2-(5-amino-1,2,4-thiadiazol-3-yl)acetamido]-3-(1-methyl-2-pyridiniothiomethyl)-3-cephem-4-carboxylate (syn isomer).

17. A compound of the claim 11 which is 7-[2-ethoxyimino-2-(5-amino-1,2,4-thiadiazol-3-yl)acetamido]-3-(1-carboxymethyl-2-pyridiniothiomethyl)-3-cephem-4-carboxylate (syn isomer).

18. A compound of claim 11 which is 7-[2-ethoxyimino-2-(5-amino-1,2,4-thiadiazol-3-yl)acetamido]-3-(1-carbamoylmethyl-2-pyridiniothiomethyl)-3-cephem-4-carboxylate (syn isomer).

19. A compound of claim 11 which is 7-[2-ethoxyimino-2-(5-amino-1,2,4-thiadiazol-3-yl)acetamido]-3-[1-(2-hydroxyethyl)-2-pyridiniothiomethyl]-3-cephem-4-carboxylate (syn isomer).

20. A compound of claim 11 which is 7-[2-ethoxyimino-2-(5-amino-1,2,4-thiadiazol-3-yl)acetamido]-3-(1-methyl-3-amino-2-pyridiniothiomethyl)-3-cephem-4-carboxylate (syn isomer).

21. A compound of claim 11 which is 7-[2-ethoxyimino-2-(5-amino-1,2,4-thiadiazol-3-yl)acetamido]-3-(1-(2-hydroxyethyl)-2,6-dimethyl-4-pyridiniothiomethyl)-3-cephem-4-carboxylate (syn isomer).

22. A compound of claim 11 which is 7-[2-ethoxyimino-2-(5-amino-1,2,4-thiadiazol-3-yl)acetamido]-3-(1-carboxymethyl-2,6-dimethyl-4-pyridiniothiomethyl)-3-cephem-4-carboxylate (syn isomer).

23. A compound of claim 11 which is 7-[2-ethoxyimino-2-(5-amino-1,2,4-thiadiazol-3-yl)acetamido]-3-(1-(2-aminoethyl)-2,6-dimethyl-4-pyridiniothiomethyl)-3-cephem-4-carboxylate (syn isomer).

24. A compound of claim 11 which is 7-[2-ethoxyimino-2-(5-amino-1,2,4-thiadiazol-3-yl)acetamido]-3-(1-(2-hydroxyethyl)-4-pyridiniothiomethyl)-3-cephem-4-carboxylate (syn isomer).

25. A compound of claim 11 which is 7-[2-(2-propynyloxyimino-2-(5-amino-1,2,4-thiadiazol-3-yl)acetamido]-3-(1-methyl-4-pyridiniothiomethyl)-3-cephem-4-carboxylate (syn isomer).

26. A compound of claim 11 which is 7-[2-allyloxyimino-2-(5-amino-1,2,4-thiadiazol-3-yl)acetamido]-3-(1-methyl-4-pyridiniothiomethyl)-3-cephem-4-carboxylate (syn isomer).

27. A compound of claim 11 which is 7-[2-(2-cyclopenten-1-yloxyimino)-2-(5-amino-1,2,4-thiadiazol-3-yl)acetamido]-3-(1-methyl-4-pyridiniothiomethyl)-3-cephem-4-carboxylate (syn isomer).

28. A compound of claim 11 which is 7-[2-methylthiomethoxyimino-2-(5-amino-1,2,4-thiadiazol-3-yl)acetamido]-3-(1-methyl-4-pyridiniothiomethyl)-3-cephem-4-carboxylate (syn isomer).

29. A compound of claim 11 which is 7-[2-methoxyimino-2-(5-amino-1,2,4-thiadiazol-3-yl)acetamido]-3-(1-methyl-4-pyridiniothiomethyl)-3-cephem-4-carboxylate (syn isomer).

30. A compound of claim 11 which is 7-[2-(1-carboxy-1-methylethoxyimino)-2-(5-amino-1,2,4-thiadiazol-3-yl)acetamido]-3-(1-methyl-4-pyridiniothiomethyl)-3-cephem-4-carboxylate (syn isomer).

31. A compound of claim 11 which is 7-[2-hydroxyimino-2-(5-amino-1,2,4-thiadiazol-3-yl)acetamido]-3-(1-methyl-4-pyridiniothiomethyl)-3-cephem-4-carboxylate (syn isomer).

* * * * *